(12) United States Patent
Isbell, Jr.

(10) Patent No.: US 11,998,195 B2
(45) Date of Patent: *Jun. 4, 2024

(54) INSTRUMENT WITH MULTIPLE ARTICULATION LOCKS

(71) Applicant: Intuitive Surgical Operations, Inc., Sunnyvale, CA (US)

(72) Inventor: Lewis R. Isbell, Jr., Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 164 days.

This patent is subject to a terminal disclaimer.

(21) Appl. No.: 17/527,364

(22) Filed: Nov. 16, 2021

(65) Prior Publication Data

US 2022/0071622 A1 Mar. 10, 2022

Related U.S. Application Data

(60) Continuation of application No. 15/647,981, filed on Jul. 12, 2017, now Pat. No. 11,234,694, which is a
(Continued)

(51) Int. Cl.
*A61B 17/068* (2006.01)
*A61B 17/00* (2006.01)
(Continued)

(52) U.S. Cl.
CPC ............ *A61B 17/068* (2013.01); *A61B 17/00* (2013.01); *A61B 17/29* (2013.01);
(Continued)

(58) Field of Classification Search
CPC ....... A61B 17/068; A61B 17/00; A61B 17/29; A61B 2090/508; A61B 2017/003;
(Continued)

(56) References Cited

U.S. PATENT DOCUMENTS 1,820,463 A 8/1931 Klein
3,060,972 A 10/1962 Sheldon
(Continued)

FOREIGN PATENT DOCUMENTS

EP 0165718 A2 12/1985
EP 0598618 A2 5/1994
(Continued)

OTHER PUBLICATIONS

Cox J.L., "The Minimally Invasive Maze-III Procedure," Operative Techniques in Thoracic and Cardiovascular Surgery, W.B. Saunders Company, 2000, vol. 5 (1), pp. 79-92.
(Continued)

*Primary Examiner* — Joshua G Kotis
*Assistant Examiner* — Scott A Howell
(74) *Attorney, Agent, or Firm* — Haynes & Boone, LLP.

(57) ABSTRACT

An articulation tool includes proximal and distal links, an elongated shaft therebetween, and first and second locks. Movement of the proximal link about proximal first and second axes causes corresponding movement of the distal link about distal first and second axes. The first and second locks have unlocked configurations in which the proximal and distal links are movable with respect to the elongated shaft about the first axes, or the second axes, respectively, and locked configurations in which the proximal and distal links are held in a fixed orientation with respect to the elongated shaft about the first axes, or the second axes, respectively. Rotation of the elongated shaft while the first and second locks are in the locked configuration and the proximal and distal links are angled with respect to the elongated shaft causes the proximal and distal links to rotate about respective longitudinal axes.

20 Claims, 42 Drawing Sheets

Related U.S. Application Data division of application No. 14/695,661, filed on Apr. 24, 2015, now Pat. No. 9,737,298, which is a continuation of application No. 13/917,928, filed on Jun. 14, 2013, now Pat. No. 9,033,960, which is a continuation of application No. 12/542,589, filed on Aug. 17, 2009, now Pat. No. 8,465,475.

(60) Provisional application No. 61/089,761, filed on Aug. 18, 2008, provisional application No. 61/089,748, filed on Aug. 18, 2008.

(51) Int. Cl.
*A61B 17/29* (2006.01)
*A61B 90/50* (2016.01)

(52) U.S. Cl.
CPC ... *A61B 2017/003* (2013.01); *A61B 2017/291* (2013.01); *A61B 2017/2927* (2013.01); *A61B 2017/2929* (2013.01); *A61B 2017/2946* (2013.01); *A61B 2090/508* (2016.02)

(58) Field of Classification Search
CPC ...... A61B 2017/291; A61B 2017/2927; A61B 2017/2929; A61B 2017/2946
See application file for complete search history.

(56) References Cited

U.S. PATENT DOCUMENTS

| | | | |
|---|---|---|---|
| 3,071,161 A | 1/1963 | Ulrich | |
| 3,190,286 A | 6/1965 | Stokes | |
| 3,557,780 A | 1/1971 | Sato | |
| 3,605,725 A | 9/1971 | Bentov | |
| 4,466,649 A | 8/1984 | Ozawa | |
| 4,489,826 A | 12/1984 | Dubson | |
| 4,580,551 A | 4/1986 | Siegmund et al. | |
| 4,700,693 A | 10/1987 | Lia et al. | |
| 4,763,669 A | 8/1988 | Jaeger | |
| 4,790,294 A | 12/1988 | Allred, III et al. | |
| 4,834,761 A | 5/1989 | Walters | |
| 4,854,626 A | 8/1989 | Duke | |
| 4,880,015 A | 11/1989 | Nierman | |
| 4,984,951 A | 1/1991 | Jameson | |
| 5,174,276 A | 12/1992 | Crockard | |
| 5,257,618 A | 11/1993 | Kondo | |
| 5,271,381 A | 12/1993 | Ailinger et al. | |
| 5,273,026 A | 12/1993 | Wilk | |
| 5,286,228 A | 2/1994 | Lee et al. | |
| 5,297,443 A | 3/1994 | Wentz | |
| 5,314,424 A | 5/1994 | Nicholas | |
| 5,322,064 A | 6/1994 | Lundquist | |
| 5,325,845 A | 7/1994 | Adair | |
| 5,330,502 A | 7/1994 | Hassler et al. | |
| 5,354,162 A | 10/1994 | Burdea et al. | |
| 5,381,782 A | 1/1995 | DeLarama et al. | |
| 5,403,342 A | 4/1995 | Tovey et al. | |
| 5,405,344 A | 4/1995 | Williamson et al. | |
| 5,425,743 A | 6/1995 | Nicholas | |
| 5,441,494 A | 8/1995 | Ortiz | |
| 5,454,827 A | 10/1995 | Aust et al. | |
| 5,476,479 A | 12/1995 | Green et al. | |
| 5,486,154 A | 1/1996 | Kelleher | |
| 5,490,819 A | 2/1996 | Nicholas et al. | |
| 5,498,256 A | 3/1996 | Furnish | |
| 5,513,827 A | 5/1996 | Michelson | |
| 5,520,678 A | 5/1996 | Heckele et al. | |
| 5,522,788 A | 6/1996 | Kuzmak | |
| 5,549,636 A | 8/1996 | Li | |
| 5,562,699 A | 10/1996 | Heimberger et al. | |
| 5,570,919 A | 11/1996 | Eusebe | |
| 5,599,151 A | 2/1997 | Daum et al. | |
| 5,609,601 A | 3/1997 | Kolesa et al. | |
| 5,618,294 A | 4/1997 | Aust et al. | |
| 5,620,415 A | 4/1997 | Lucey et al. | |
| 5,624,398 A | 4/1997 | Smith et al. | |
| 5,626,608 A | 5/1997 | Cuny et al. | |
| 5,632,432 A | 5/1997 | Schulze et al. | |
| 5,643,294 A | 7/1997 | Tovey et al. | |
| 5,647,743 A | 7/1997 | Schmitt | |
| 5,702,408 A * | 12/1997 | Wales | A61B 17/07207 606/205 |
| 5,704,534 A | 1/1998 | Huitema et al. | |
| 5,713,505 A | 2/1998 | Huitema | |
| 5,716,352 A | 2/1998 | Viola et al. | |
| 5,759,151 A | 6/1998 | Sturges | |
| 5,772,578 A | 6/1998 | Heimberger et al. | |
| 5,792,164 A | 8/1998 | Lakatos et al. | |
| 5,807,376 A | 9/1998 | Viola et al. | |
| 5,813,813 A | 9/1998 | Daum et al. | |
| 5,823,066 A | 10/1998 | Huitema et al. | |
| 5,827,323 A | 10/1998 | Klieman et al. | |
| 5,836,960 A | 11/1998 | Kolesa et al. | |
| 5,845,540 A | 12/1998 | Rosheim | |
| 5,846,183 A | 12/1998 | Chilcoat | |
| 5,873,817 A | 2/1999 | Kokish et al. | |
| 5,899,425 A | 5/1999 | Corey, Jr. et al. | |
| 5,916,146 A | 6/1999 | Allotta et al. | |
| 5,916,147 A | 6/1999 | Boury | |
| 5,921,956 A | 7/1999 | Grinberg et al. | |
| 5,938,678 A | 8/1999 | Zirps et al. | |
| 5,947,984 A | 9/1999 | Whipple | |
| 5,961,532 A | 10/1999 | Finley et al. | |
| 6,019,722 A | 2/2000 | Spence et al. | |
| 6,050,996 A | 4/2000 | Schmaltz et al. | |
| 6,161,543 A | 12/2000 | Cox et al. | |
| 6,250,532 B1 | 6/2001 | Green et al. | |
| 6,270,453 B1 | 8/2001 | Sakai | |
| 6,464,704 B2 | 10/2002 | Schmaltz et al. | |
| 6,471,641 B2 | 10/2002 | Sakamoto | |
| 6,471,696 B1 | 10/2002 | Berube et al. | |
| 6,482,149 B1 | 11/2002 | Torii | |
| 6,491,626 B1 | 12/2002 | Stone et al. | |
| 6,571,042 B1 | 5/2003 | Kordahi | |
| 6,626,824 B2 | 9/2003 | Ruegg et al. | |
| 6,635,071 B2 | 10/2003 | Boche et al. | |
| 6,638,213 B2 | 10/2003 | Ogura et al. | |
| 6,638,287 B2 | 10/2003 | Danitz et al. | |
| RE38,335 E | 11/2003 | Aust et al. | |
| 6,641,528 B2 | 11/2003 | Torii | |
| 6,644,532 B2 | 11/2003 | Green et al. | |
| 6,666,854 B1 | 12/2003 | Lange | |
| 6,669,254 B2 | 12/2003 | Thom et al. | |
| 6,676,676 B2 | 1/2004 | Danitz et al. | |
| 6,682,541 B1 | 1/2004 | Gifford, III et al. | |
| 6,743,239 B1 | 6/2004 | Kuehn et al. | |
| 6,746,443 B1 | 6/2004 | Morley et al. | |
| 6,749,560 B1 | 6/2004 | Konstorum et al. | |
| 6,752,823 B2 | 6/2004 | Prestel | |
| 6,764,445 B2 | 7/2004 | Ramans et al. | |
| 6,773,327 B1 | 8/2004 | Felice et al. | |
| 6,817,972 B2 | 11/2004 | Snow | |
| 6,824,548 B2 | 11/2004 | Smith et al. | |
| 6,843,794 B2 | 1/2005 | Sixto, Jr. et al. | |
| 6,858,005 B2 | 2/2005 | Ohline et al. | |
| 6,902,560 B1 | 6/2005 | Morley et al. | |
| 6,942,613 B2 | 9/2005 | Ewers et al. | |
| 6,945,979 B2 | 9/2005 | Kortenbach et al. | |
| 6,960,162 B2 | 11/2005 | Saadat et al. | |
| 6,960,163 B2 | 11/2005 | Ewers et al. | |
| 6,976,969 B2 | 12/2005 | Messerly | |
| 6,994,700 B2 | 2/2006 | Elkins et al. | |
| 7,138,976 B1 | 11/2006 | Bouzit et al. | |
| 7,159,750 B2 | 1/2007 | Racenet et al. | |
| 7,480,600 B2 | 1/2009 | Massie et al. | |
| 7,494,039 B2 | 2/2009 | Racenet et al. | |
| 7,553,275 B2 | 6/2009 | Padget et al. | |
| 7,615,067 B2 | 11/2009 | Lee et al. | |
| 7,726,537 B2 | 6/2010 | Olson et al. | |
| 7,828,808 B2 | 11/2010 | Hinman et al. | |
| 7,862,554 B2 | 1/2011 | Hegeman et al. | |
| 8,100,824 B2 | 1/2012 | Hegeman et al. | |
| 8,292,154 B2 | 10/2012 | Marczyk | |
| 8,465,475 B2 | 6/2013 | Isbell, Jr. | |

(56) References Cited

U.S. PATENT DOCUMENTS

| | | |
|---|---|---|
| 8,490,851 B2 | 7/2013 | Blier et al. |
| 8,568,390 B2 | 10/2013 | Mueller |
| 8,770,669 B2 | 7/2014 | Wachsmann et al. |
| 9,033,960 B2 | 5/2015 | Isbell, Jr. |
| 9,700,334 B2 | 7/2017 | Hinman et al. |
| 9,737,298 B2 | 8/2017 | Isbell, Jr. et al. |
| 11,234,694 B2 | 2/2022 | Isbell, Jr. |
| 2001/0023313 A1 | 9/2001 | Ide |
| 2001/0042766 A1 | 11/2001 | Ming-Shun |
| 2002/0096177 A1 | 7/2002 | Toti et al. |
| 2002/0111604 A1 | 8/2002 | Doyle et al. |
| 2002/0156497 A1 | 10/2002 | Nagase et al. |
| 2002/0161281 A1 | 10/2002 | Jaffe et al. |
| 2002/0177750 A1 | 11/2002 | Pilvisto et al. |
| 2003/0036748 A1 | 2/2003 | Cooper et al. |
| 2003/0050649 A1 | 3/2003 | Brock et al. |
| 2003/0078644 A1 | 4/2003 | Phan |
| 2003/0109898 A1 | 6/2003 | Schwarz et al. |
| 2003/0114838 A1 | 6/2003 | Oneill et al. |
| 2003/0135204 A1 | 7/2003 | Lee et al. |
| 2003/0149338 A1 | 8/2003 | Francois et al. |
| 2003/0153902 A1 | 8/2003 | Doyle et al. |
| 2003/0229271 A1 | 12/2003 | Briscoe et al. |
| 2003/0233026 A1 | 12/2003 | Saadat et al. |
| 2004/0054322 A1 | 3/2004 | Vargas |
| 2004/0138529 A1 | 7/2004 | Wiltshire et al. |
| 2004/0138700 A1 | 7/2004 | Cooper et al. |
| 2004/0236316 A1 | 11/2004 | Danitz et al. |
| 2005/0090809 A1 | 4/2005 | Cooper et al. |
| 2005/0096694 A1 | 5/2005 | Lee |
| 2005/0107667 A1 | 5/2005 | Danitz et al. |
| 2005/0119527 A1 | 6/2005 | Banik et al. |
| 2005/0251112 A1 | 11/2005 | Danitz et al. |
| 2005/0273085 A1 | 12/2005 | Hinman et al. |
| 2006/0009759 A1 | 1/2006 | Chrisitian et al. |
| 2006/0020287 A1 | 1/2006 | Lee et al. |
| 2006/0036255 A1 | 2/2006 | Pond et al. |
| 2006/0058582 A1 | 3/2006 | Maahs et al. |
| 2006/0094931 A1 | 5/2006 | Danitz et al. |
| 2006/0111210 A1* | 5/2006 | Hinman ............... A61B 17/29 474/206 |
| 2006/0111615 A1 | 5/2006 | Danitz et al. |
| 2006/0111616 A1 | 5/2006 | Danitz |
| 2006/0199999 A1 | 9/2006 | Ikeda et al. |
| 2006/0201130 A1* | 9/2006 | Danitz ............... A61B 17/2909 59/78.1 |
| 2007/0225562 A1 | 9/2007 | Spivey et al. |
| 2007/0250113 A1* | 10/2007 | Hegeman ............ A61B 1/0055 606/207 |
| 2007/0276430 A1* | 11/2007 | Lee .................... A61B 1/00071 606/205 |
| 2007/0282371 A1* | 12/2007 | Lee ................... A61B 17/29 606/205 |
| 2007/0287993 A1* | 12/2007 | Hinman ............. A61B 1/00042 606/1 |
| 2008/0065116 A1* | 3/2008 | Lee ................... A61B 17/2909 606/208 |
| 2008/0188869 A1 | 8/2008 | Weitzner et al. |
| 2008/0188871 A1 | 8/2008 | Smith et al. |
| 2008/0255588 A1* | 10/2008 | Hinman ............ A61B 17/2909 606/139 |
| 2008/0255608 A1* | 10/2008 | Hinman ............... A61B 17/00 606/205 |
| 2008/0262538 A1 | 10/2008 | Danitz et al. |
| 2010/0041945 A1* | 2/2010 | Isbell, Jr. ............ A61B 17/29 600/142 |
| 2017/0325812 A1 | 11/2017 | Isbell, Jr. |
| 2019/0128347 A1 | 5/2019 | Leimbach et al. |

FOREIGN PATENT DOCUMENTS

| | | |
|---|---|---|
| EP | 0836833 A2 | 4/1998 |
| EP | 1132041 A2 | 9/2001 |
| EP | 1395398 B1 | 1/2006 |
| JP | H06262549 A | 9/1994 |
| JP | 2001299768 A | 10/2001 |
| WO | WO-200110292 A1 | 2/2001 |
| WO | WO-200213682 A1 | 2/2002 |
| WO | WO-2004019769 A1 | 3/2004 |
| WO | WO-2005067785 A1 | 7/2005 |
| WO | WO-2004105578 A3 | 11/2005 |
| WO | WO-2005120327 A3 | 3/2006 |
| WO | WO-2006057699 A1 | 6/2006 |
| WO | WO-2006057700 A1 | 6/2006 |
| WO | WO-2006057702 A2 | 6/2006 |
| WO | WO-2006073581 A2 | 7/2006 |

OTHER PUBLICATIONS

Danitz, David J.; U.S. Appl. No. 12/766,820 entitled "Articulating mechanism with bifurcating control," filed Apr. 23, 2010 (NVRE701-504/US).

Danitz, David J.; U.S. Appl. No. 12/766,822 entitled "Articulating catheters," filed Apr. 23, 2010 (NVRE701-506/US).

Danitz, David J.; U.S. Appl. No. 12/766,825 entitled "Articulating endoscopes," filed Apr. 23, 2010 (NVRE701-507/US).

Danitz, David J.; U.S. Appl. No. 12/766,827 entitled "Articulating retractors," filed Apr. 23, 2010 (NVRE701-508/US).

Danitz et al.; U.S. Appl. No. 12/766,818 entitled "Articulating instruments with joystick control," filed Apr. 23, 2010 (NVRE701-503/US).

Hinman, Cameron; U.S. Appl. No. 12/508,478 entitled "Articulating mechanism," filed Jul. 23, 2009 (NVRE714-201/US).

Hinman et al.; U.S. Appl. No. 12/725,377 entitled " Articulating mechanism with flex-hinged links," filed Mar. 16, 2010 (NVRE706-202/US).

Hinman et al.; U.S. Appl. No. 12/816,359 entitled "Link systems and articulation mechanisms for remote manipulation of surgical or diagnostic tools," filed Jun. 15, 2010. (NVRE706-303/US).

International Search Report for Application No. PCT/US2005/018145 (WO2005120326), dated Feb. 20, 2006, 5 pages.

Prasad S.M., et al., "Epicardial Ablation on the Beating Heart: Progress Towards an Off-Pump Maze Procedure," The Heart Surgery Forum, Forum Multimedia Publishing, LLC, 2002, vol. 5 (2), pp. 100-104.

Simha P.M., et al., "The Electrocautery Maze—How I Do It," The Heart Surgery Forum, Forum Multimedia Publishing, LLC, 2001, vol. 4 (4), pp. 340-345.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

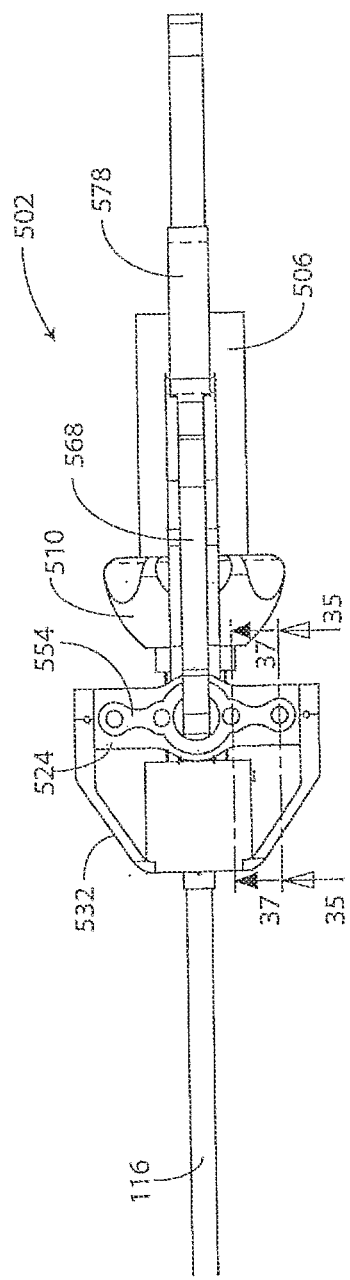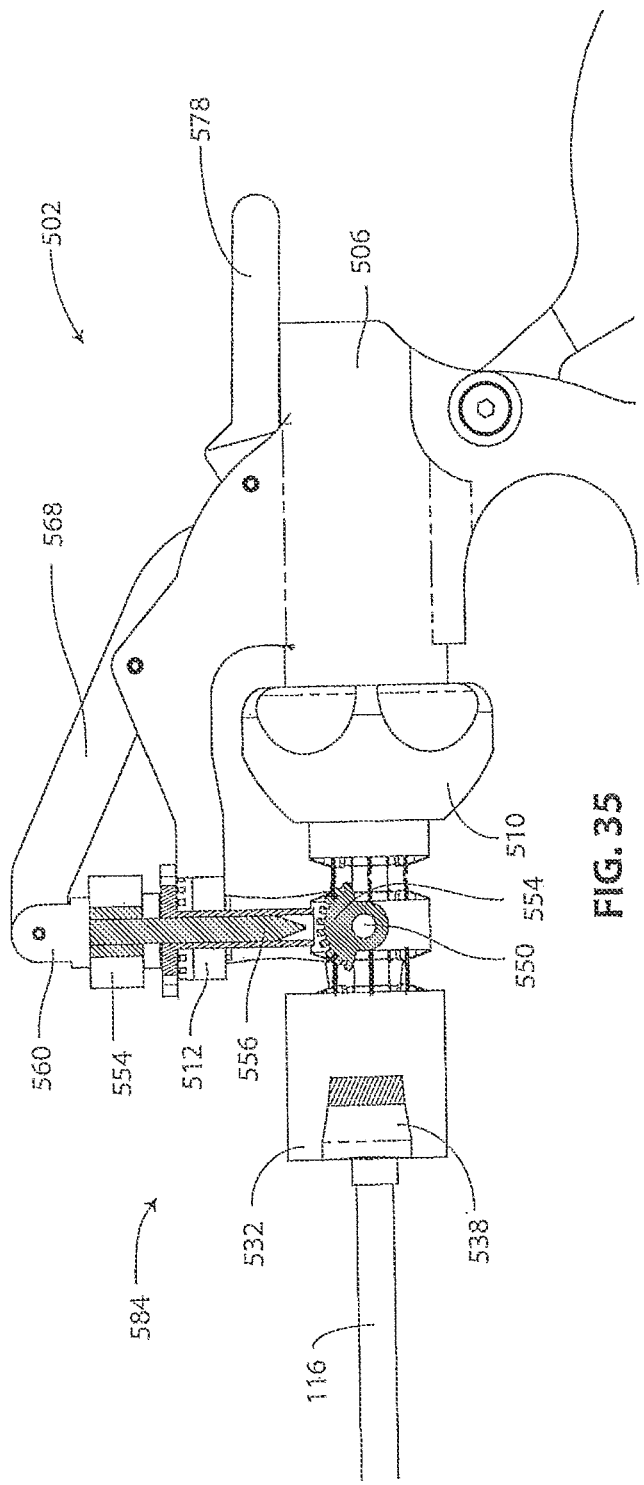

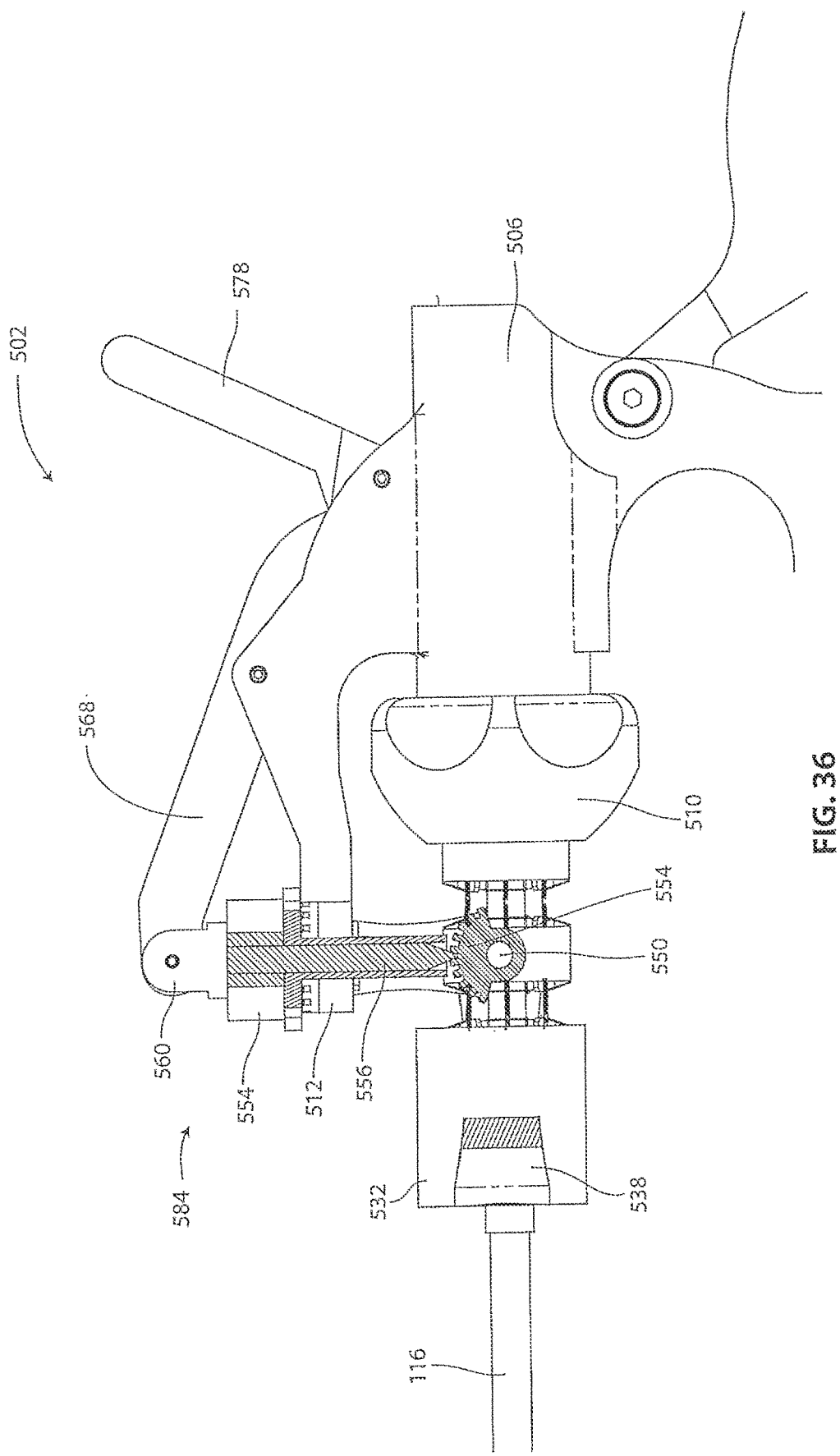

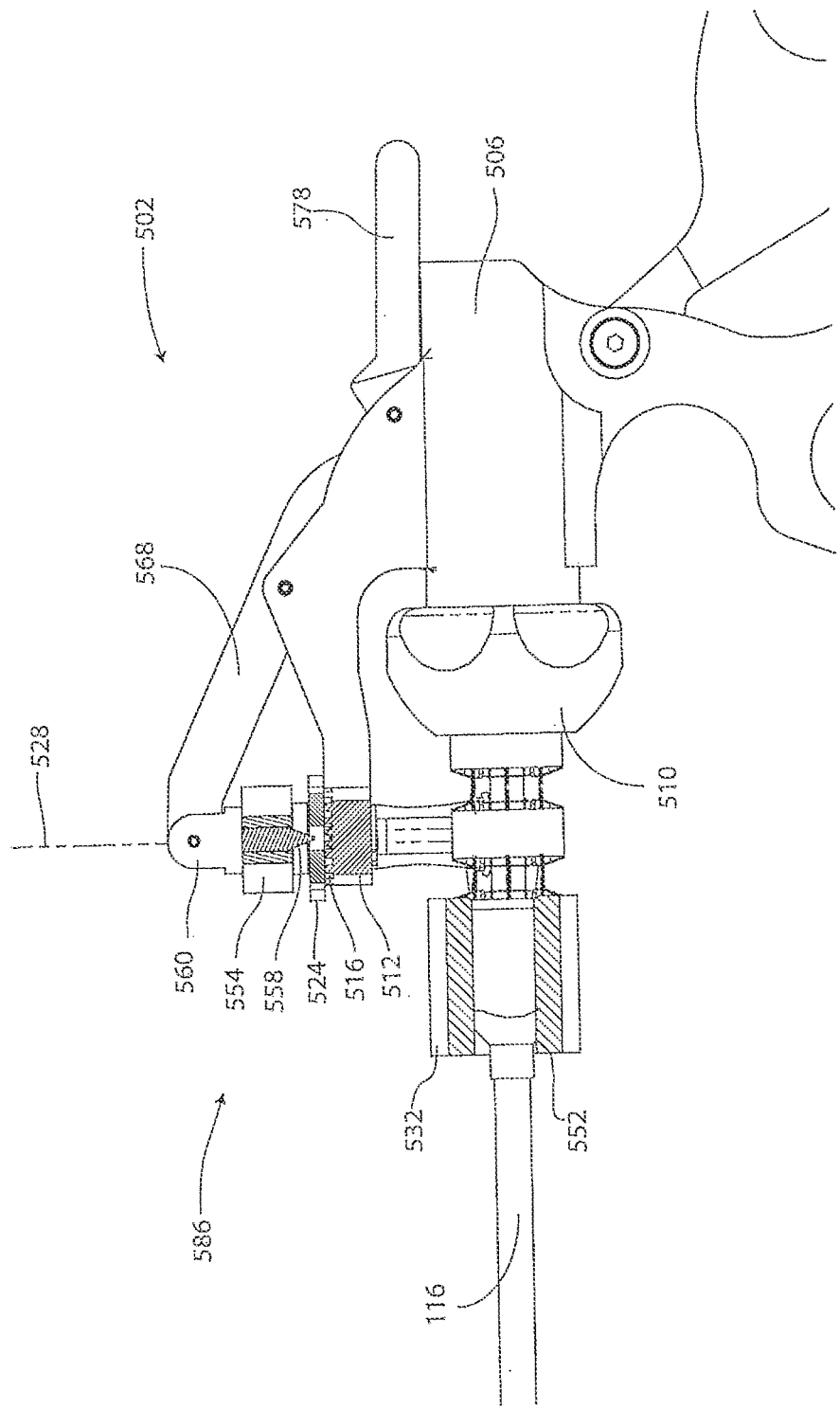

INSTRUMENT WITH MULTIPLE ARTICULATION LOCKS

CROSS REFERENCE TO RELATED APPLICATIONS

This application is a continuation of U.S. patent application Ser. No. 15/647,981, filed Jul. 12, 2017, which is a divisional of U.S. patent application Ser. No. 14/695,661, filed Apr. 24, 2015 and issued as U.S. Pat. No. 9,737,298, which is a continuation of U.S. patent application Ser. No. 13/917,928, filed Jun. 14, 2013 and issued as U.S. Pat. No. 9,033,960, which is a continuation of U.S. patent application Ser. No. 12/542,589, filed Aug. 17, 2009 and issued as U.S. Pat. No. 8,465,475, which claims the benefit of U.S. provisional application Ser. Nos. 61/089,748 and 61/089,761, both filed Aug. 18, 2008, the full disclosures of which (including all references incorporated by reference therein) are incorporated by reference herein, in their entireties.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to articulating mechanisms and applications thereof, including the remote guidance and manipulation of surgical or diagnostic tools.

BACKGROUND OF THE INVENTION

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy, as well as newer procedures in natural orifice transluminal endoscopic surgery ("NOTES"). Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding issues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Steerable catheters are also well known for both diagnostic and therapeutic applications. Similar to endoscopes, such catheters include tips that can be directed in generally limited ranges of motion to navigate a patient's vasculature. There have been many attempts to design endoscopes and catheters with improved steerability. For example, U.S. Pat. No. 3,357,780 to Sato; U.S. Pat. No. 5,271,381 to Ailinger et al.; U.S. Pat. No. 5,916,146 to Alotta et al.; U.S. Pat. No. 6,270,453 to Sakai, and U.S. Pat. No. 7,147,650 to Lee describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), by a pulley mechanism (Sato), or by manipulation of complementary portions (Lee), U.S. Pat. No. 5,916,147 to Boury et al. discloses a steerable catheter having four wires that run within the catheter wall. Each wire terminates at a different part of the catheter. The proximal ends of the wires extend loosely from the catheter so that the physician may pull them. The physician is able to shape and thereby steer the catheter by selectively placing the wires under tension.

Recently, surgical instruments, including minimally invasive surgical instruments, have been developed that are more ergonomic and which have a wider range of motion and more precise control of movement. These instruments may include mechanisms that articulate using a series of links coupled with one or more sets of tension bearing members, such as cables. As with conventional instruments-used in minimally invasive surgery, rotation of the shaft and end effector with respect to the handle is also an important feature of cable and link type instruments to aid with dissecting, suturing, retracting, knot tying, etc. With the increasing complexity associated with surgical procedures that these instruments are used to perform, further improvements in the features and design of surgical instruments are desirable.

SUMMARY OF THE INVENTION

According to some aspects of the present invention, an articulating tool is provided with an articulation lock. Methods of using such a tool are also provided. Embodiments of the articulating tool may be appropriate for single or multiple uses, including medical uses such as diagnostic and surgical uses. Embodiments of the articulating tool include a shaft having a proximal and a distal end, an articulation mechanism, and an elongated guide located along at least a portion of the shaft, the guide being configured to guide the tension bearing members. The articulation mechanism may include a movable proximal element disposed at the proximal end of the shaft, a movable distal element disposed at the distal end of the shaft, and a plurality of tension bearing members extending between the proximal and distal elements such that movement of the movable proximal element with respect to the shaft causes a corresponding movement of the movable distal element with respect to the shaft.

In some embodiments of the invention, a tool is provided with proximal, central and distal portions, an articulation mechanism, and first and second articulation locks. In these embodiments, the central portion is pivotably coupled to the proximal portion and the distal portion is pivotably coupled to the central portion. The articulation mechanism may be configured to manipulate an angular orientation of the distal portion relative to the central portion. The articulation mechanism may include a pair of links, the pair comprising a proximal link on the proximal portion of the tool and a distal link on the distal portion of the tool. The articulator mechanism may be adapted such that movement of the proximal link causes corresponding relative movement of the distal link. In these embodiments, the first articulation lock has an engaged position and a disengaged position.

When in the engaged position, the first articulation lock impedes movement of the proximal link relative to the central portion about a yaw axis, and corresponding relative movement of the distal link. The second articulation lock also has an engaged position and a disengaged position. When in the engaged position, the second articulation lock impedes movement of the proximal link relative to the central portion about a pitch axis, and corresponding relative movement of the distal link.

In some of the above embodiments, the tool further includes an actuator configured to move both the first and the second articulation locks into their engaged positions at substantially the same time. The actuator may include a lever located atop the proximal portion. In some embodiments, the proximal portion of the tool includes a handle. The handle and the actuator may be adapted to be operated by a single hand.

In some embodiments, a rotation mechanism is provided on the proximal portion of the tool configured to drive rotation of the central portion relative to the proximal portion when at least one of the articulation locks is in the engaged position. The first articulation lock may include a section pivotably coupled to the proximal portion and the second articulation lock may include a section pivotably coupled to the first articulation lock. The second articulation lock may include a member that slidably receives a part of the central portion.

In some embodiments, the tool includes a grasper located on the distal portion and a handle located on the proximal portion. The handle in these embodiments may be configured to operate the grasper. The tool may further include one or more of the following members located on the distal portion of the tool: scissors, a cautery element, an ultrasound element, laser optics, illumination optics, a light source, and/or a microphone.

In some embodiments, methods of using the above tools are provided. Some of the methods include the step of moving the first and the second articulation locks of the tool into their engaged positions. In some embodiments, the first and the second articulation locks are moved into their engaged positions at substantially the same time. In some embodiments, the method further includes the step of articulating the distal portion of the tool into an off-axis position by moving the proximal portion before moving the articulation locks into their engaged positions. Some methods include the step of rotating the central portion of the tool about a longitudinal axis after moving the articulation locks into their engaged positions. Some methods include the step of manipulating a handle located on the proximal portion to operate a grasper located on the distal portion of the tool. In some of these methods, the central portion of the tool may be rotated about a longitudinal axis after moving the grasper to a dosed position and moving the articulation locks into their engaged positions.

BRIEF DESCRIPTIONS OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which are briefly described below.

FIG. 1A is an obliquely distal-looking perspective view of an exemplary articulating device having a handle and an end effector. FIG. 1B is a detailed view of the circled portion of FIG. 1A, which includes proximal links and bushings FIG. 2A shows the device of FIG. 1A in a proximal-looking view, with the handle and end effector in an articulated position. FIG. 2B is a detailed view of the circled portion of FIG. 2A, which includes distal links and bushings.

FIG. 4 is a right side perspective view of a first embodiment of an articulation lock shown on the proximal end of an articulating tool.

FIG. 5 is a front perspective view of the tool of FIG. 4.

FIG. 6 is the left side perspective view of the tool of FIG. 4.

FIG. 7 is a top view of the tool of FIG. 4.

FIG. 8 is the bottom perspective view of the tool of FIG. 4.

FIG. 9 is an exploded view of the tool of FIG. 4.

FIG. 10 is a bottom perspective view showing the base component of the tool of FIG. 4.

FIG. 11 is a front perspective view showing the rotating clamp component of the tool of FIG. 4.

FIG. 12 is a side cross-sectional view taken along the centerline of the tool of FIG. 4.

FIG. 13 is a top cross-sectional view of the tool of FIG. 4 taken along line 13-13 in FIG. 12.

FIG. 14 is an end cross-sectional view of the tool of FIG. 4 taken along line 14-14 in FIG. 12.

FIG. 34 is a top view showing the proximal end of the tool of FIG. 24.

FIG. 35 is a cross-sectional view of the tool of FIG. 24 taken along line 35-35 in FIG. 34 showing a second articulation lock in an unlocked state.

FIG. 36 is a cross-sectional view of the tool of FIG. 24 taken along line 35-35 in FIG. 34 showing a second articulation lock in a locked state.

FIG. 37 is a cross-sectional view of the tool of FIG. 24 taken along line 37-37 in FIG. 34 showing a first articulation lock in an unlocked state.

DETAILED DESCRIPTION OF THE INVENTION

Figure 1:
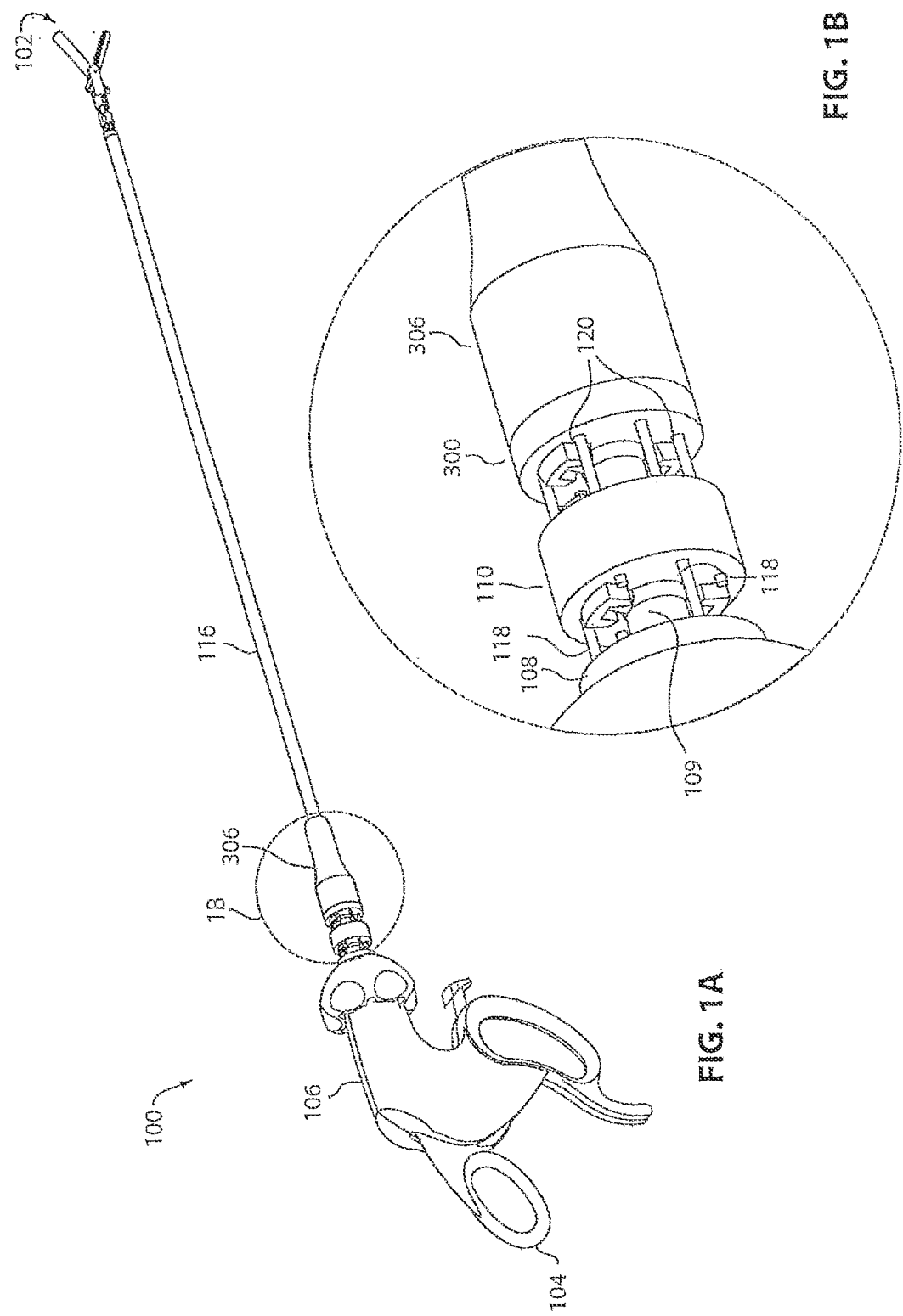

Articulating tools are described in U.S. Pat. No. 7,090,637; US 2005/0107667; US 2005/0273084; US 2005/0273085; US 2006/0111209, US 2006/0111210, and US 2006/0111615. The articulating mechanisms of the tools described in those publications use multiple pairs of segments or links controlled, e.g., by multiple sets of cables, as well as tools that have a single pair of links, connected by a single set of cables, such as those described in U.S. Pat. No. 5,916,146. Depending upon the specific design of the device, the links can be discrete segments (as described, e.g., in U.S. Pat. No. 7,090,637) or discrete portions of a flexible segment (as described, e.g., in US 2005/0273085). The instrument may also include steerable or controllable links, e.g., as described in US 2005/0273084, US 2006/0111209 and US 2006/0111210. The devices of this invention may include optional end effectors at their distal ends and end effector actuators supported by a handle at their proximal ends. When using such articulating instruments, a user may manipulate the proximal end of the instrument, thereby moving one or more distal links of the articulation mechanism. Aspects of the present invention may be used in any of these and in other articulating mechanisms.

FIGS. 1A and 2A show an exemplary articulatable tool 100 with an end effector 102 at its distal end and an end effector actuator 104 within a handle 106 at its proximal end: FIG. 1A shows the tool in a neutral or non-articulated configuration, while FIG. 2A shows the tool in an articulated position or configuration. FIG. 1B shows detail (encircled in FIG. 1A) of the proximal links of the tool. FIG. 2B shows detail (encircled in FIG. 2A) of the distal links of the tool. Instrument 100 may be used, e.g., in a laparoscopic procedure requiring grasping or cutting within a patient. Exemplary embodiments of the tool 100 may also be useful in endoscopic procedures, particularly when, as in some embodiments, the tool has a flexible shaft. Still other embodiments may be used for percutaneous procedures, such as a catheter. Still other embodiments include devices that are directed toward natural orifice transluminal endoscopic surgery ("NOTES"). Embodiments of the invention may include a wide variety of tools, some with medical or diagnostic purposes, and others that are applied to other types of tasks where the articulational capabilities of the tool provide benefit.

Proximal articulation links 108 and 110 extend distally from handle 106, and distal articulation links 112 and 114 extend proximally from end effector 102. Proximal link 108 is a spindle and is connected to and moves with handle 106 Likewise, distal link 112 is connected to and moves with end effector 102. An elongated shaft 116 is disposed between the proximal links and the distal links; in some embodiments the shaft is rigid, in other embodiments the shaft maybe flexible.

A set of tension bearing elements or control cables 118 is attached to proximal link 108, extends through proximal link 110, shaft 116 and distal link 114 and is attached to distal link 112, as shown in FIGS. 1A and 1B. A second set of tension hearing element or control cables 120 is attached to proximal link 110, extends through shaft 116 and is attached to distal link 114. In this embodiment, there are three control cables 118 in the first set and three control cables 120 in the second set. It should be appreciated, however, that other numbers of control cables may be used to connect corresponding proximal and distal links. In addition, tension bearing elements other than cables may be used to connect corresponding links. In some embodiments, the tension members may comprise cables that are capable of only transmitting tension between the links. In other embodiments, the tension members may comprise Nitinol wires, rods or other elements capable of transmitting both tension and compression. In these latter embodiments, a link may be alternately pushed and pulled by at least one tension member. In some embodiments, one set of control cables, such as cables 120, may be eliminated to provide an instrument with a single pair of connected links. What is meant by the word "connected" is that the cable(s) are attached to or are terminated in a pair of links to allow one link to drive another link. This is distinguished from any intermediate links that are not "connected". In these intermediate links, the cables merely extend through the links in a slidable fashion, and the cables do not drive movement of the links.

As shown in FIGS. 1A, 1B, 2A, and 2B, movement of handle 106 and proximal link 108 with respect to proximal link 110 moves end effector 102 and distal link 112 in a relative and corresponding manner. Likewise, movement of proximal link 110 with respect to shaft 116 moves distal link 114 with respect to shaft 116 in a relative and corresponding manner, also as shown in FIG. 2. This relative articulation movement provides a way for a user to remotely manipulate the end effector through movement of the handle. It should be understood that the proximal and distal links can be connected by the tension bearing elements so as to move at the same direction with respect to the shaft (thereby providing a mirror image movement) or in opposite directions with respect to the shaft, depending on whether the tension bearing elements connect the corresponding links on the opposite sides or on the same sides of the links, respectively. In addition, the degree of relative movement can be determined by the relative diameters of the cables' connections to corresponding links as well as through the use and specific design of bushings or spacer links separating the connected proximal and distal links. For example, in the embodiment shown in FIGS. 1-3, the cables' radial spacing on the proximal links is about three times greater than their radial spacing on the distal links. This means that a movement of about 5.degree. in a proximal link will cause a corresponding movement of about 15.degree. in a distal link. Further details of these links are provided in US2005/0273085, which is hereby incorporated by this reference.

In the embodiment illustrated in FIG. 1, the end effector 102 is a pair of jaws. Actuation force is transmitted from end effector actuator 104 through a transmission that includes a linearly movable rod and a rotatable rod actuator (not shown). Other end effectors (surgical, diagnostic, etc.) and end effector actuators may be used with an articulating tool constructed according to this invention. In some embodiments, the distal links themselves can comprise an end effector, such as, for example, a retractor. The movable rod may comprise any flexible material; in some embodiments Nitinol offers particular advantages as it is sufficiently flexible to accommodate articulation, and yet can still carry a compressive load sufficiently, for example, to be able to push open an end effector, such as a set of jaws. In some embodiments, a series of proximal links, themselves, can comprise a "handle" with no other rigid handle being provided. In other words, the proximal links may be formed into a particular shape which is emulated by a corresponding series of distal links. More details of such embodiments are provided in U.S. Pat. No. 7,090,637.

Figure 2:
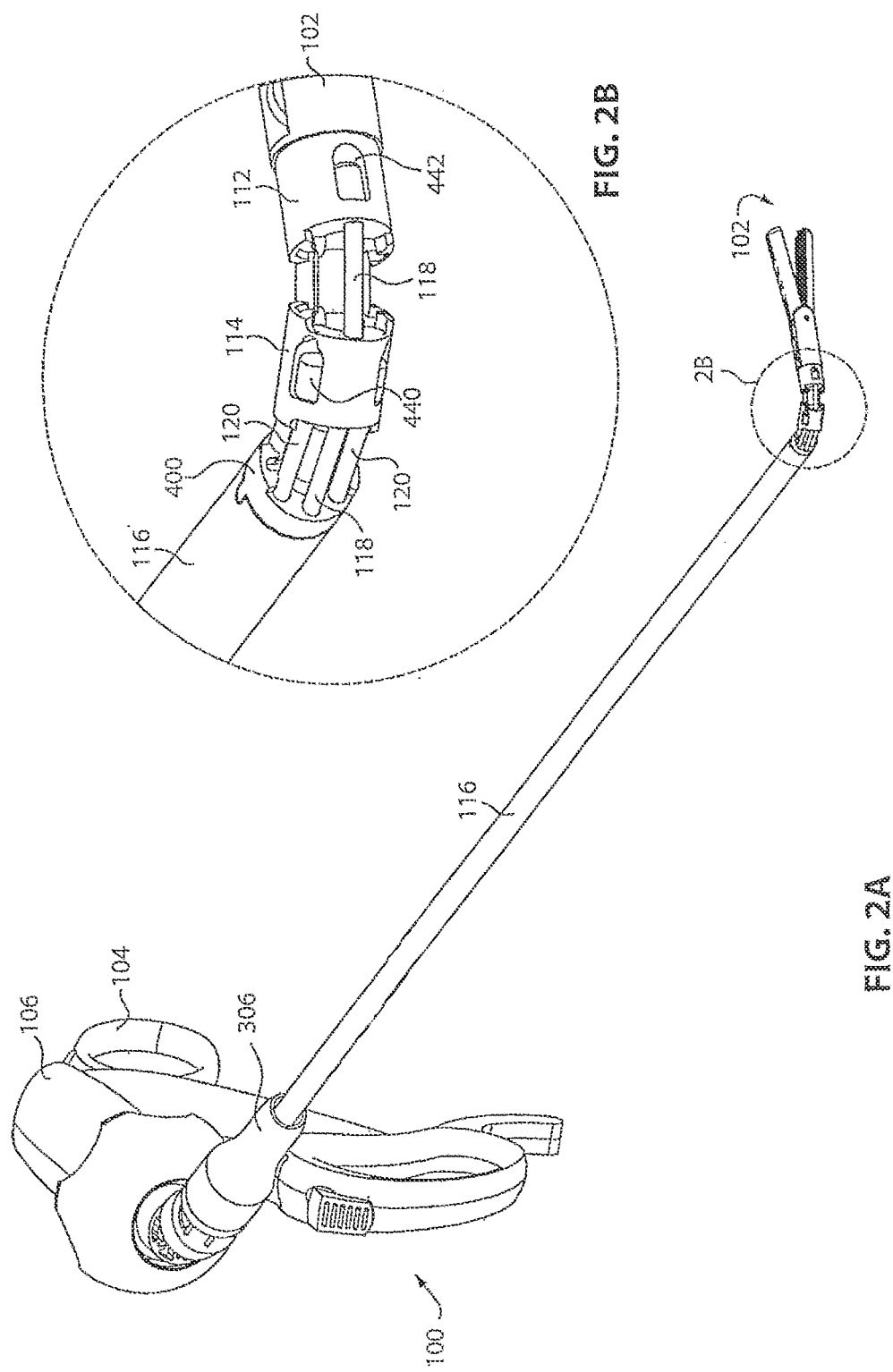
Figure 3:
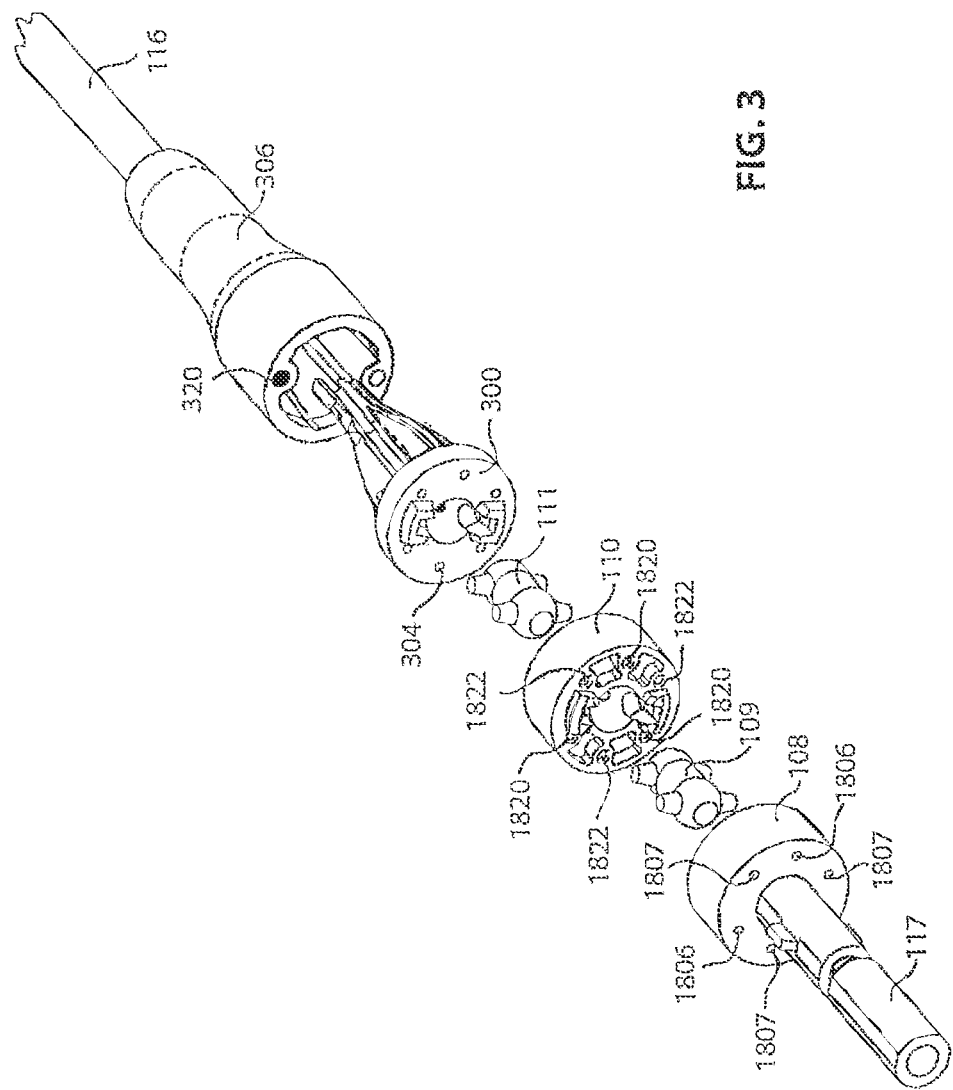
FIG. 3 is an exploded perspective view of certain proximal components of the articulating device of FIGS. 1 and 2.

FIG. 3 shows an exploded view of certain proximal components of the articulating tool. The tension members have been omitted for clarity. As shown, a double headed bushing 109 is disposed between links 108 and 110, and another bushing 111 is disposed between links 110 and a proximal end cap 300. The interaction of bushings 109 and 111 with links 108 and 110 and with proximal end cup 300 is described in more detail in U.S. 2005/0273084, U.S. 2006/0111209, and U.S. 2006/0111210. If the tension bearing cables 118 and 120 were shown in FIG. 3 as they are in FIGS. 1 and 2, the proximal ends of the three cables 118 would terminate in or otherwise be "connected" to link 108 within openings 1806 of link 108, and the cables would pass through openings 1820 in link 110 and openings 304 in end cap 300 before catering shaft 116. Likewise, the proximal ends of three cables 120 would terminate in or otherwise be "connected" to link 110 within openings 1822 of link 110 and would pass through openings 304 in proximal end cap 300 before entering shaft 116. A tapered end cap housing or cover 306 may be rigidly fixed to shaft 116 to provide a transition front end cap 300 to shaft 116.

As previously noted, device 100 shown in FIGS. 1-3 includes two pairs of links, each interconnected by its own set of tension members. Specifically, one pair is formed by proximal link 108 and distal link 112 which are interconnected by tension members 118, and another pair is formed by proximal link 110 and distal link 114 which are interconnected by tension members 120. In other embodiments, only a single pair of links interconnected by a single set of tension members is used. In yet other embodiments, three or more pairs of links may be used, each interconnected by a discrete set of tension members. In some embodiments, instead of a set of tension members, only a single tension member may be used between a pair of links, such as when the tension member is capable of also transmitting compression between the links.

As shown in FIG. 3, proximal links 108 and 110 are separated by bushing 109, and proximal link 110 is separated from proximal end cap 300 by bushing 111. Proximal bushings 109 and 110 each have a convex spherical component or ball located at each of their ends. Mating concave recesses are formed in proximal links 108 and 110 and in proximal end cap 300 for receiving a portion of the ball ends of the bushings. With this arrangement, proximal links 108 and 110 pivot relative to one another about two pivot points (i.e. about the centers of the two ball ends of bushing 109). Similarly, proximal link 110 and end cap 300 pivot relative to one another about two pivot points (i.e. about the centers of the two ball ends of bushing 111). In other embodiments (not shown), links may pivot relative to one another about a single pivot point. In the embodiment shown in FIG. 3, protruding pin features are located on opposite sides of each ball and are pivotably received within mating slots located in the concave recesses. This pin and slot configuration allows torque to be transmitted across the four proximal spherical joints. Distal links 112 and 114, and distal end cap 400 are separated by bushings in a similar arrangement.

Referring to FIGS. 4-14, the proximal portion of an instrument constructed according to aspects of the present invention is shown and described. The device of this first exemplary articulation locking embodiment may have a distal portion (not shown) similar to that shown in FIGS. 1-2 and described above. The proximal portion of the device includes an articulation lock. In an unlocked position, shaft 116 and end effector 102 (both shown in FIGS. 1-2) may be articulated relative to handle 1 in a manner similar to that previously described. The articulation lock may then be moved to a locked position in which the proximal end of shaft 116 is held in a fixed orientation relative to handle 1. In this locked state, the proximal links of the articulation mechanism are prevented from pivoting. Because the proximal and distal links are interconnected by tension members such as cables, this in turn prevents pivoting of the distal links and locks end effector 102 in a fixed orientation relative to the distal end of shaft 116. However, by rotating knob 7, shaft 116 may be caused to rotate about its longitudinal axis even when in a locked position, and end effector 102 is caused to rotate about its own longitudinal axis while being held in a fixed orientation. This feature allows a surgeon to, for example, lock the orientation of an end effector 102 when holding a needle, but rotate end effector 102 about its axis for "throwing a stitch." The orientation of the end effector 102 may be locked and the end effector rotated regardless of whether the axis of the end effector 102 is aligned with the axis of the shaft 116 or is articulated to be at an angle to the shaft.

Figure 4:
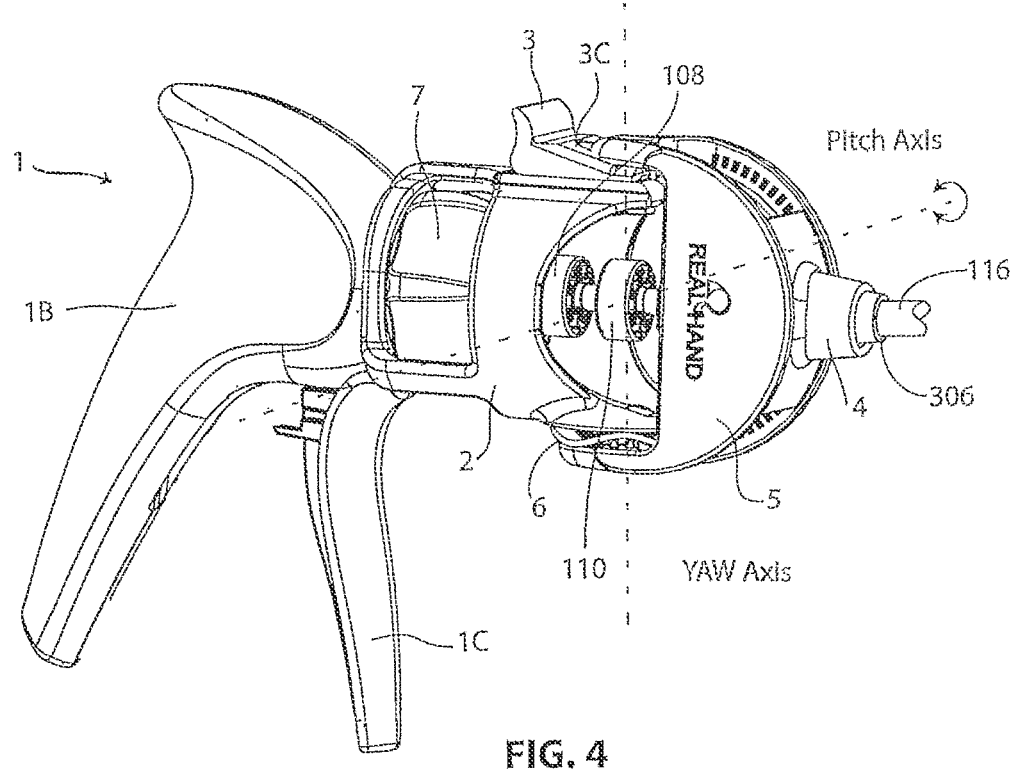
FIGS. 4-14 show a first exemplary embodiment of an articulation lock.
Figure 5:
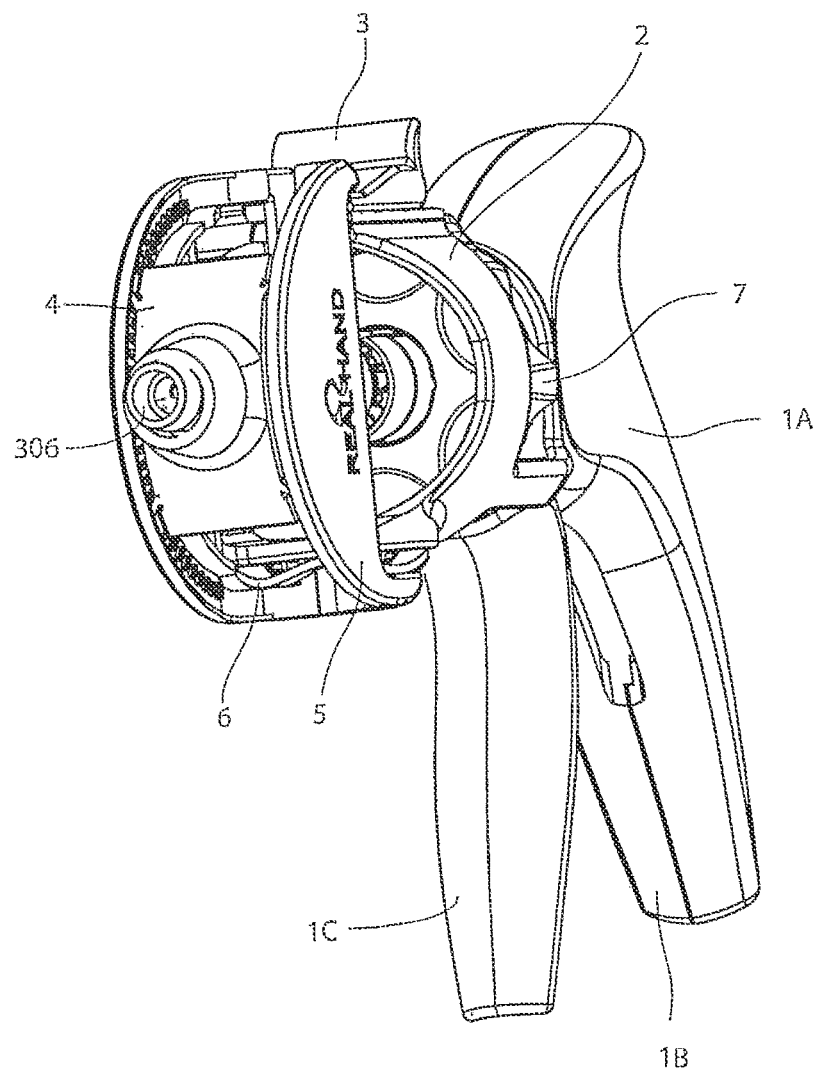
Figure 6:
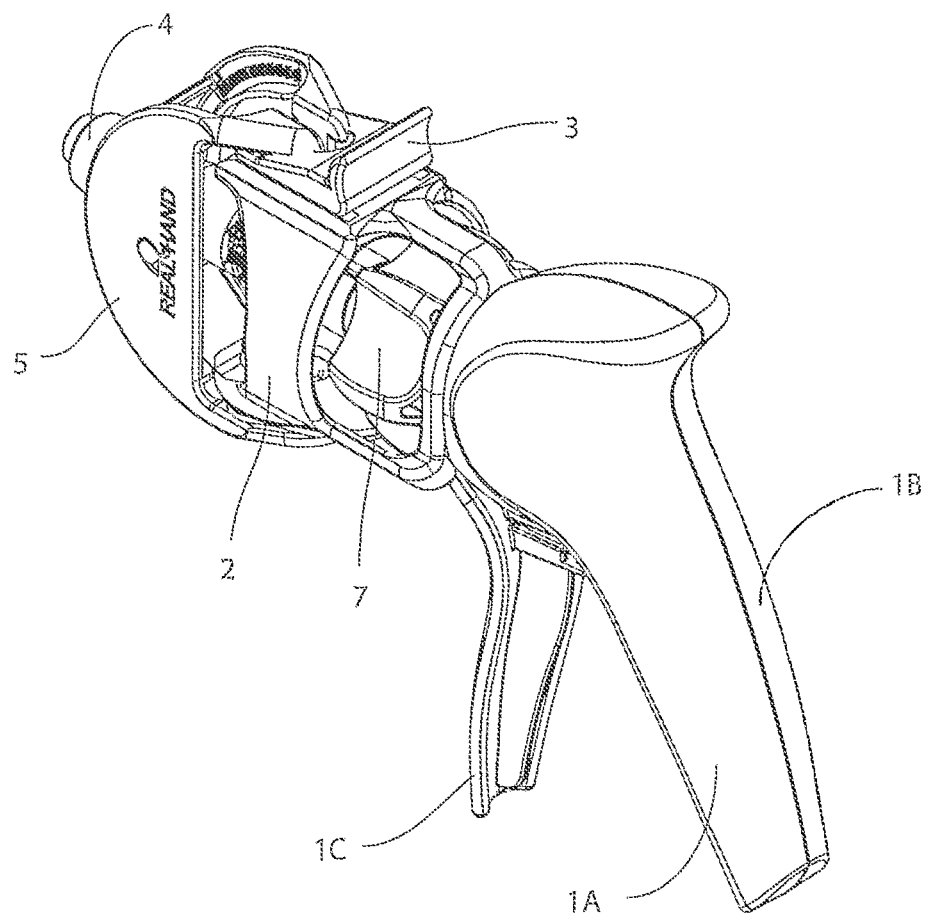
Figure 7:
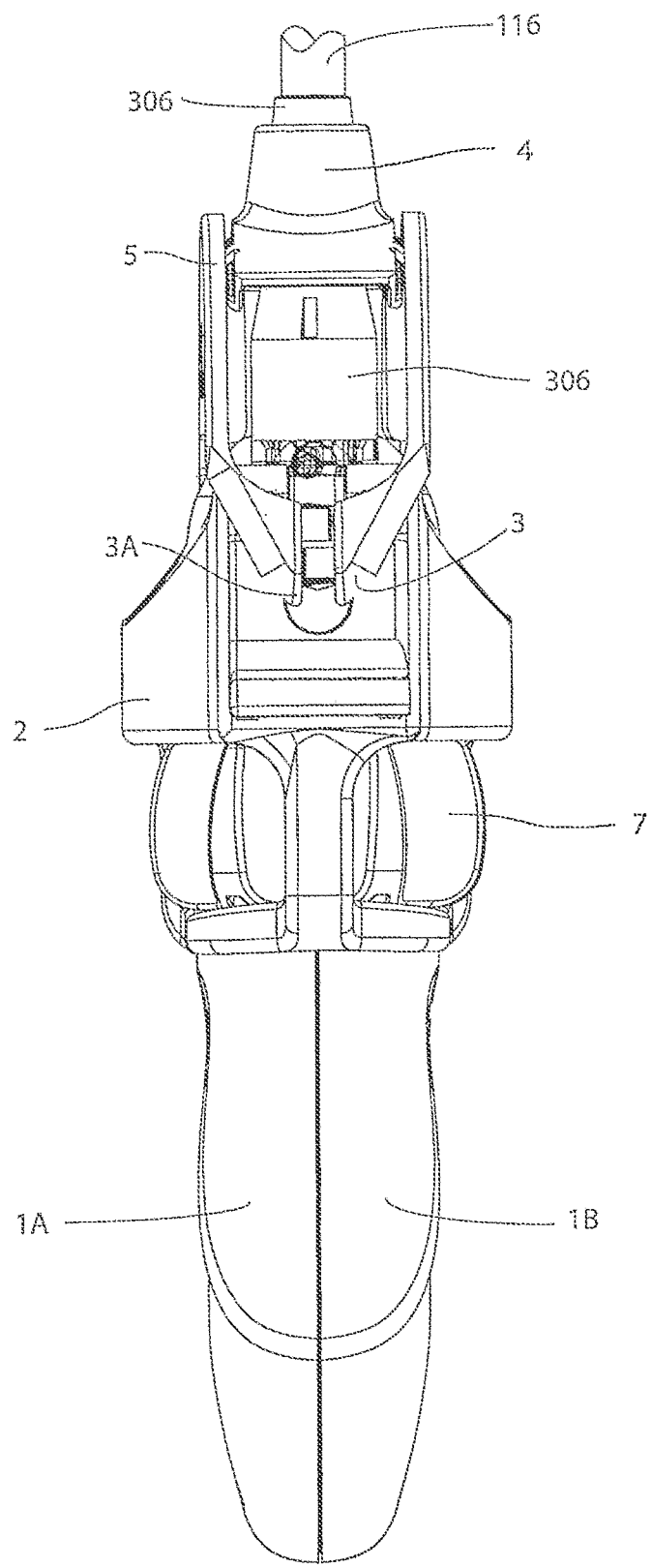
Figure 8:
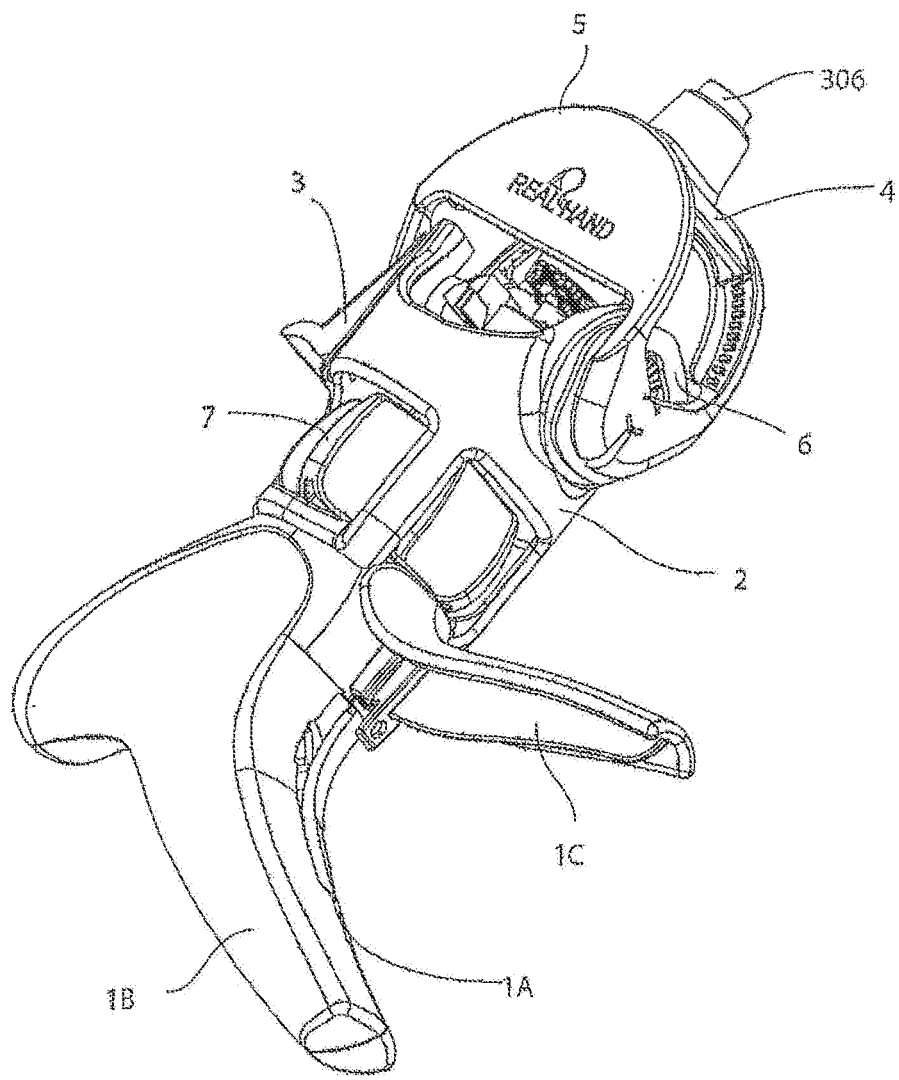
Figure 9:
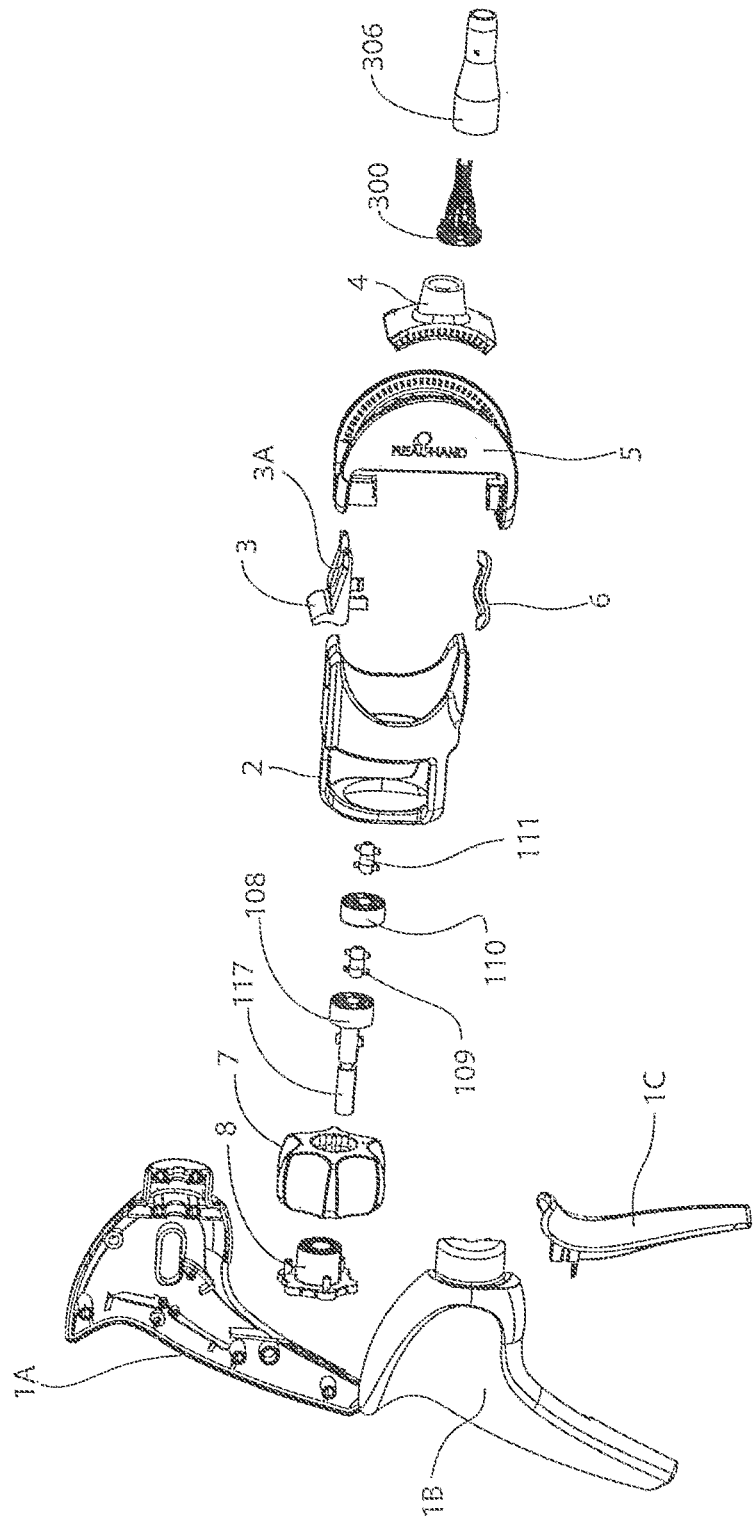
Figure 10:
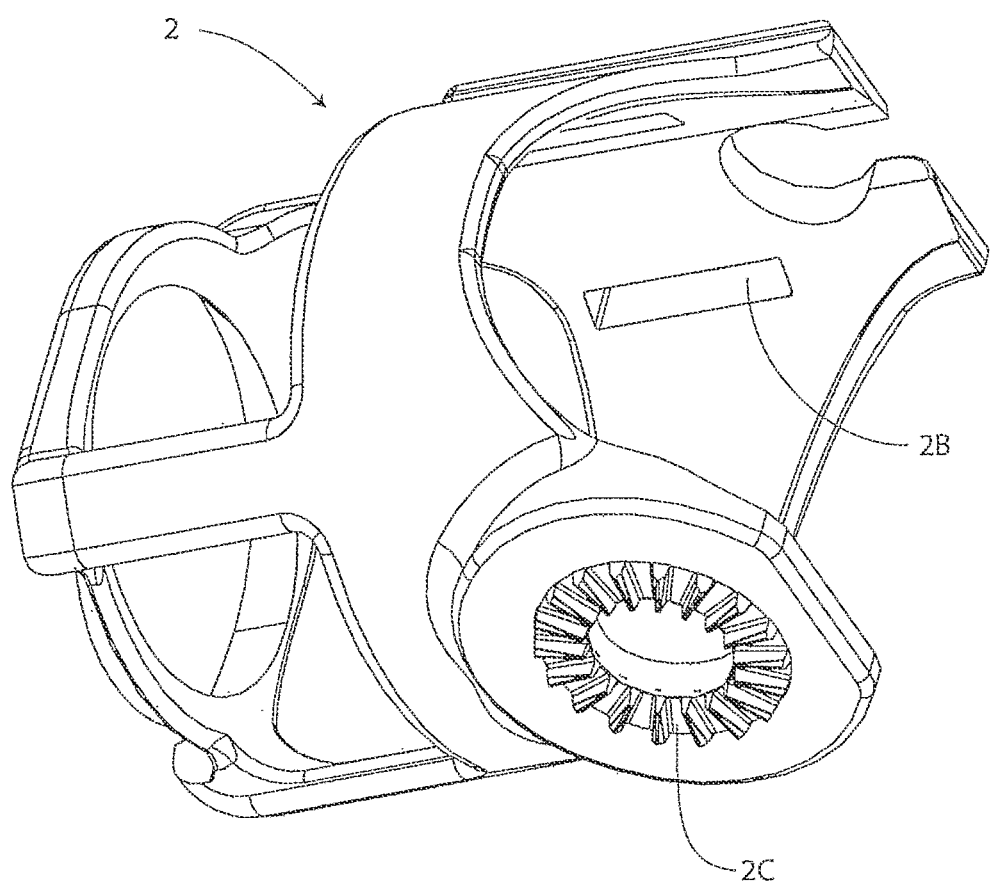

In the first exemplary embodiment shown in FIGS. 4-14, the instrument includes a base 2 rigidly attached to handle 1. Rotating clamp 5 is pivotably connected to base 2 allowing clamp 5 to rotate about a yaw axis, as shown in FIG. 4. Turret cover 4 is slidably connected to clamp 5 such that it can rotate in an arc about a pitch axis, as also shown in FIG. 4. End cap housing 306 is affixed to the proximal end of shaft 116 (not shown in FIG. 4) and is slidably held within a central aperture of turret cover 4 such that end cap housing 306 may axially translate and rotate. With this arrangement, shaft 116 may be articulated about the pitch and yaw axes with respect to handle 1.

Figure 11:
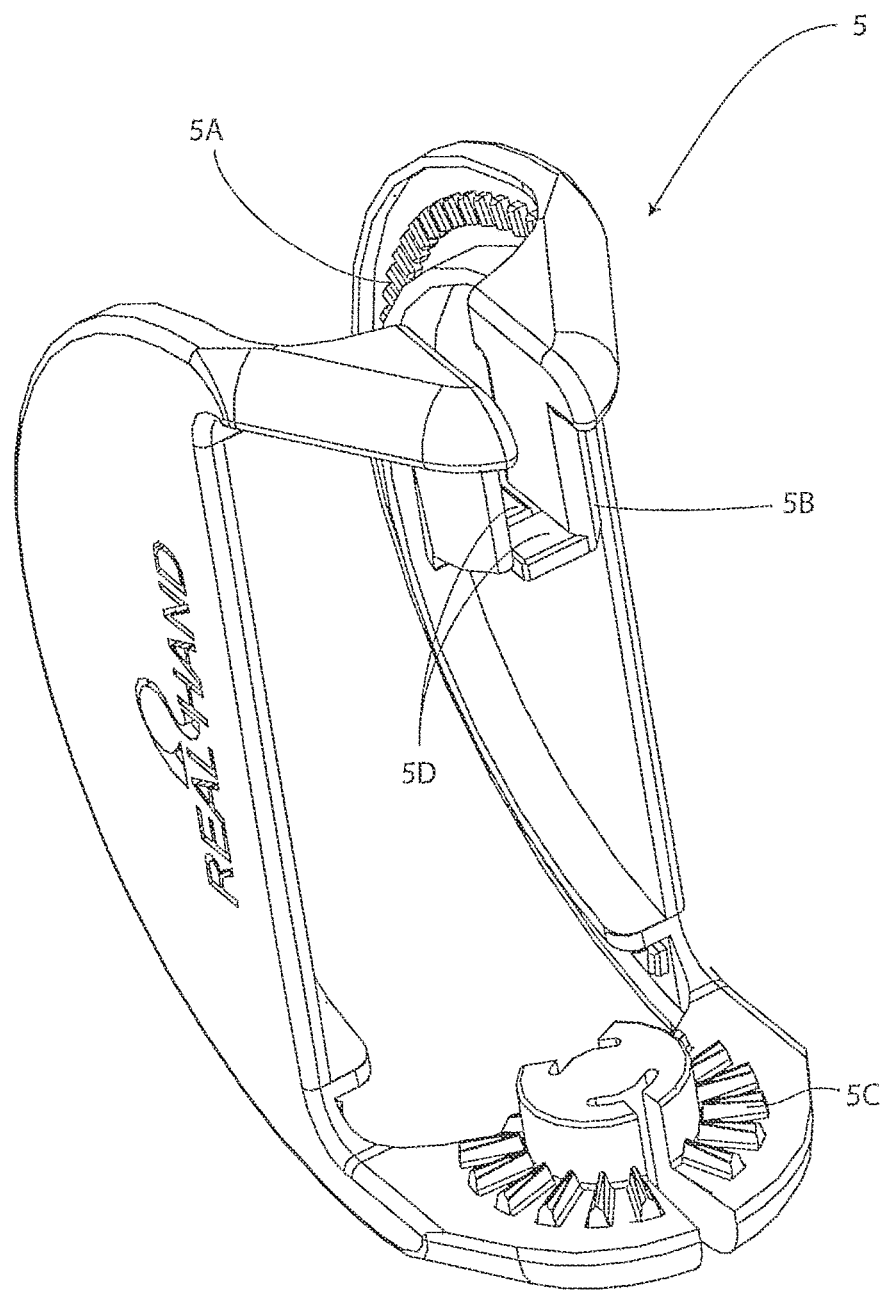
Figure 12:
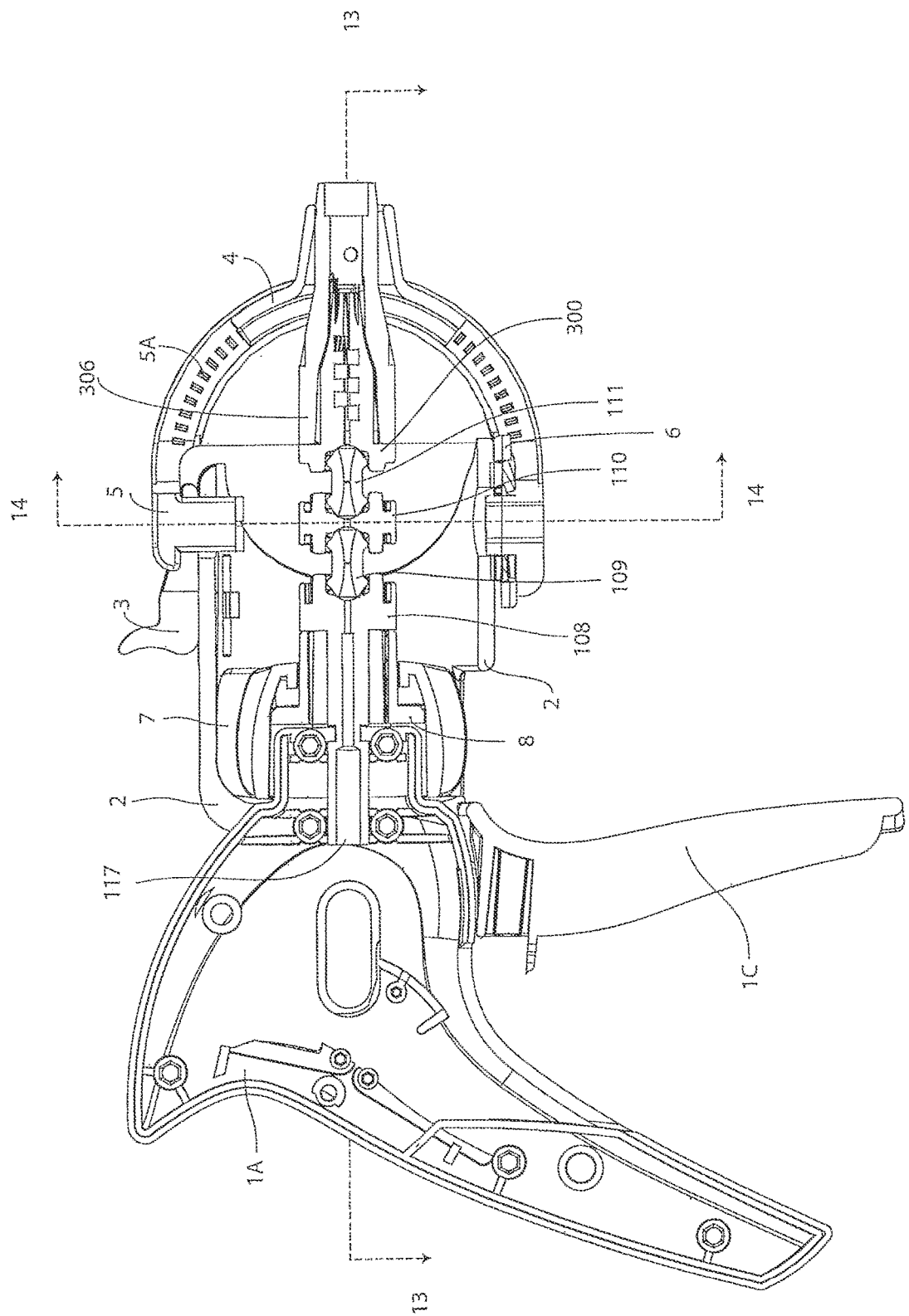
Figure 13:
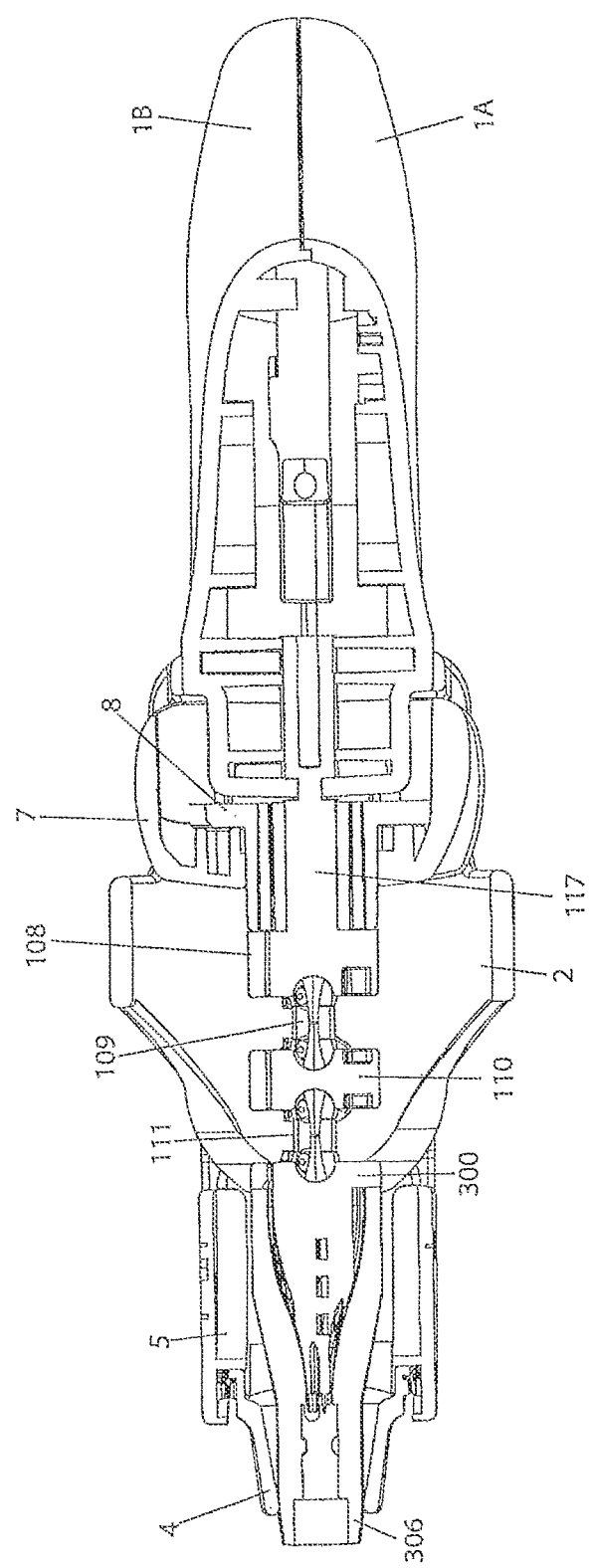
Figure 14:
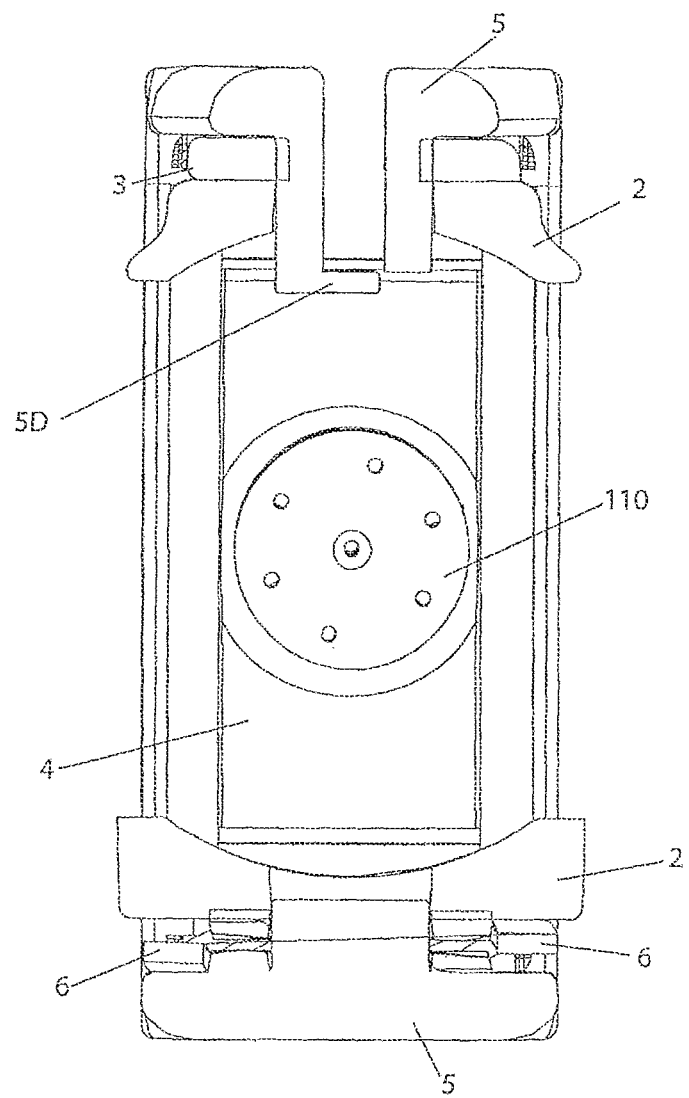
Figure 15:
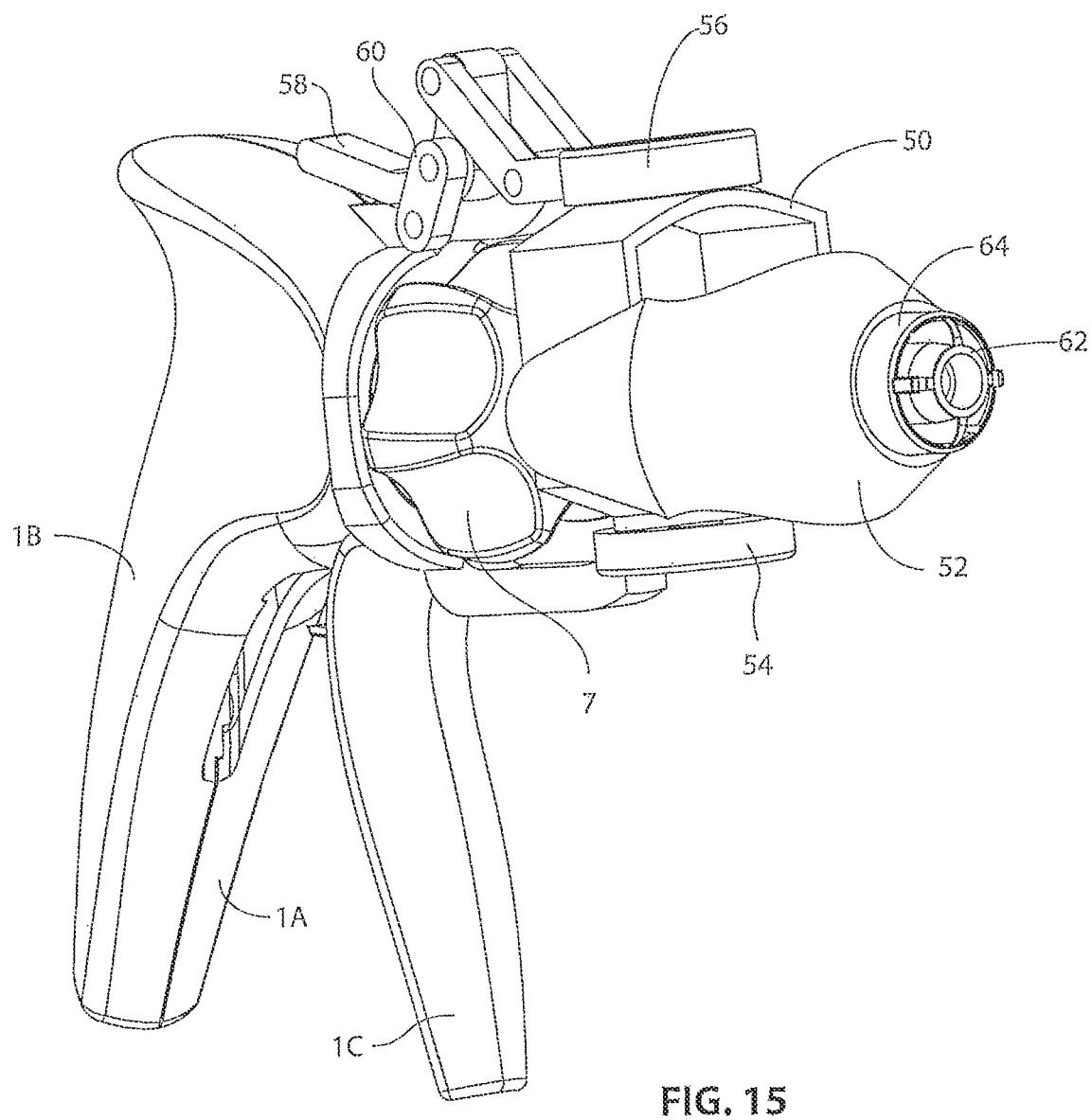
FIG. 15 is a right side perspective view of a second embodiment of an articulation lock shown on the proximal end of an articulating tool.

Lock 3 may be moved between an unlocked proximal position (as shown in FIG. 4) and a distal locked position. As lock 3 is moved distally into the locked position, ramp 3C lifts rotating clamp 5 against the downward bias of wave spring 6 to engage rotating clamp teeth 5C (best seen in FIG. 11) with axis teeth 2C of body 2 (best seen in FIG. 10), thereby locking rotation of rotating clamp 5 about the yaw axis. Clamp 3 also includes an angled groove 3A. As clamp 3 is moved distally into the locked position, groove 3A causes the top portions of the sides of rotating clamp 5 to be squeezed together. The bottom portions of the sides of rotating clamp 5 are held at a fixed distance, but they act as a flexible hinge so that the top portions can be squeezed together. This movement engages teeth 5A located on the outer periphery of both sides of rotating clamp 5 (as best seen in FIGS. 11 and 12) with teeth 4B on both sides of turret cover 4, thereby preventing rotation of turret cover 4 and shaft 116 about the pitch axis. Thus, when lock 3 is in the locked distal position, shaft 116 (shown in FIGS. 1 and 2) is locked from articulating with respect to handle 1 but may be rotated by turning knob 7 as previously described. Again, when the orientation of shaft 116 is locked with respect to handle 1, the proximal links are locked, which in turn lock the distal links and end effector from pivoting. When lock 3 is returned to the unlocked proximal position, shaft 116 may be rotated and/or articulated.

Referring to FIGS. 15-23, the proximal portion of a second articulation lock embodiment is shown and described. As in the first embodiment, the device of this second embodiment may have a distal portion (not shown) similar to that shown in FIGS. 1-2 and described above. The proximal portion of the device includes an articulation lock. In an unlocked position, shaft 116 and end effector 102 (both shown in FIGS. 1-2) may be articulated relative to handle 1 in a manner similar to that previously described. The articulation lock may then be moved to a locked position in which the proximal end of shaft 116 is held in a fixed orientation relative to handle 1. This in turn locks end effector 102 in a fixed orientation relative to the distal end of shaft 116. In this locked state, the proximal links of the articulation mechanism are prevented from pivoting. Because the proximal and distal links are interconnected, by tension members such as cables, this in turn prevents pivoting of the distal links and locks end effector 102 in a fixed orientation relative to the distal end of shaft 116. However, by rotating knob 7, shaft 116 may be caused to rotate about its longitudinal axis even when in a locked position, and end effector 102 is caused to rotate about its own longitudinal axis while being held in a fixed orientation. This feature allows a surgeon to, for example, lock the orientation of an end effector 102 when holding a needle, but rotate end effector 102 about its axis for "throwing a stitch." The orientation of the end effector 103 may be locked and the end effector rotated regardless of whether the axis of the end effector 102 is aligned with the axis of the shaft 116 or is articulated to be at an angle to the shaft.

Figure 16:
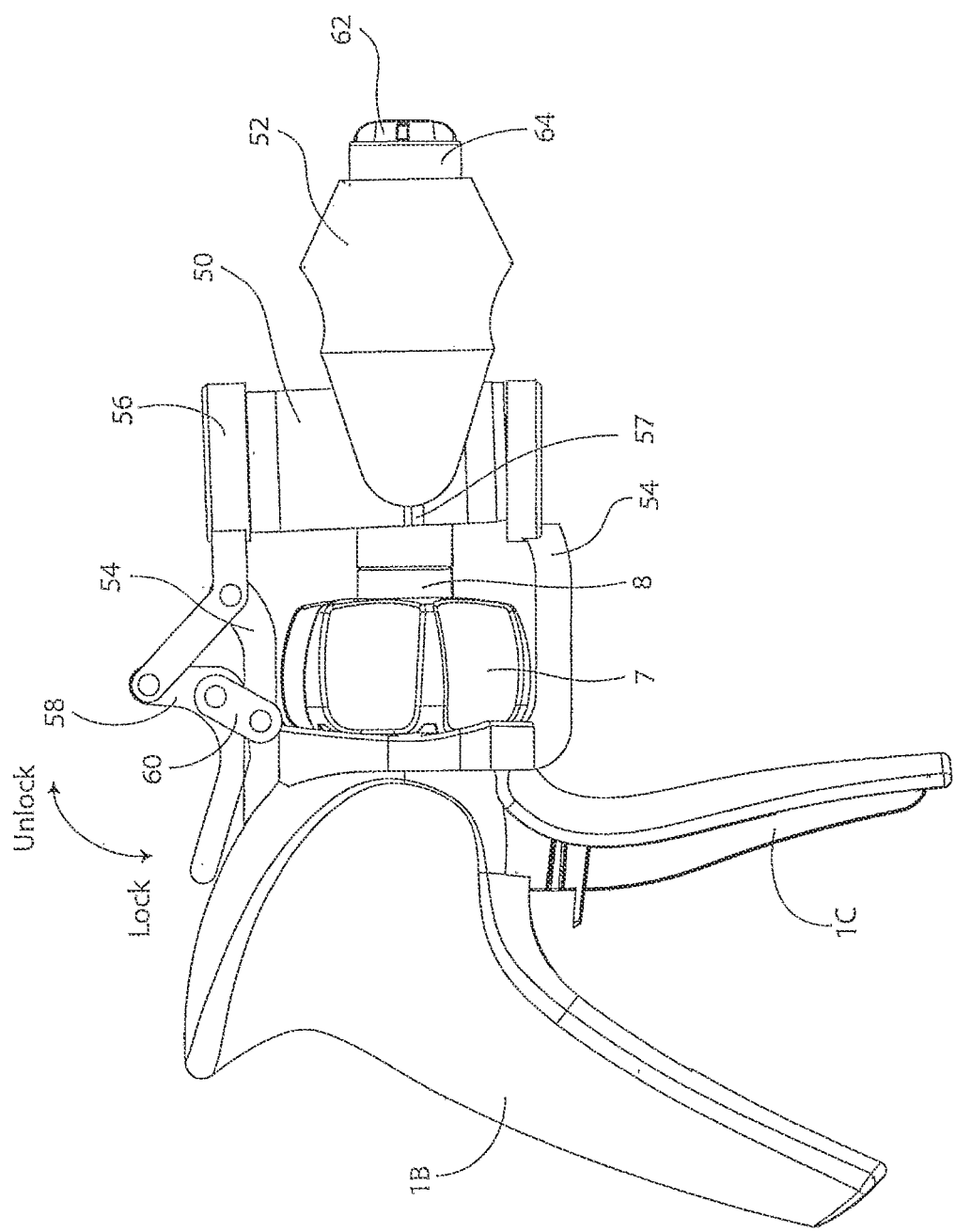
FIG. 16 is a right side plan view of the tool of FIG. 15.
Figure 17:
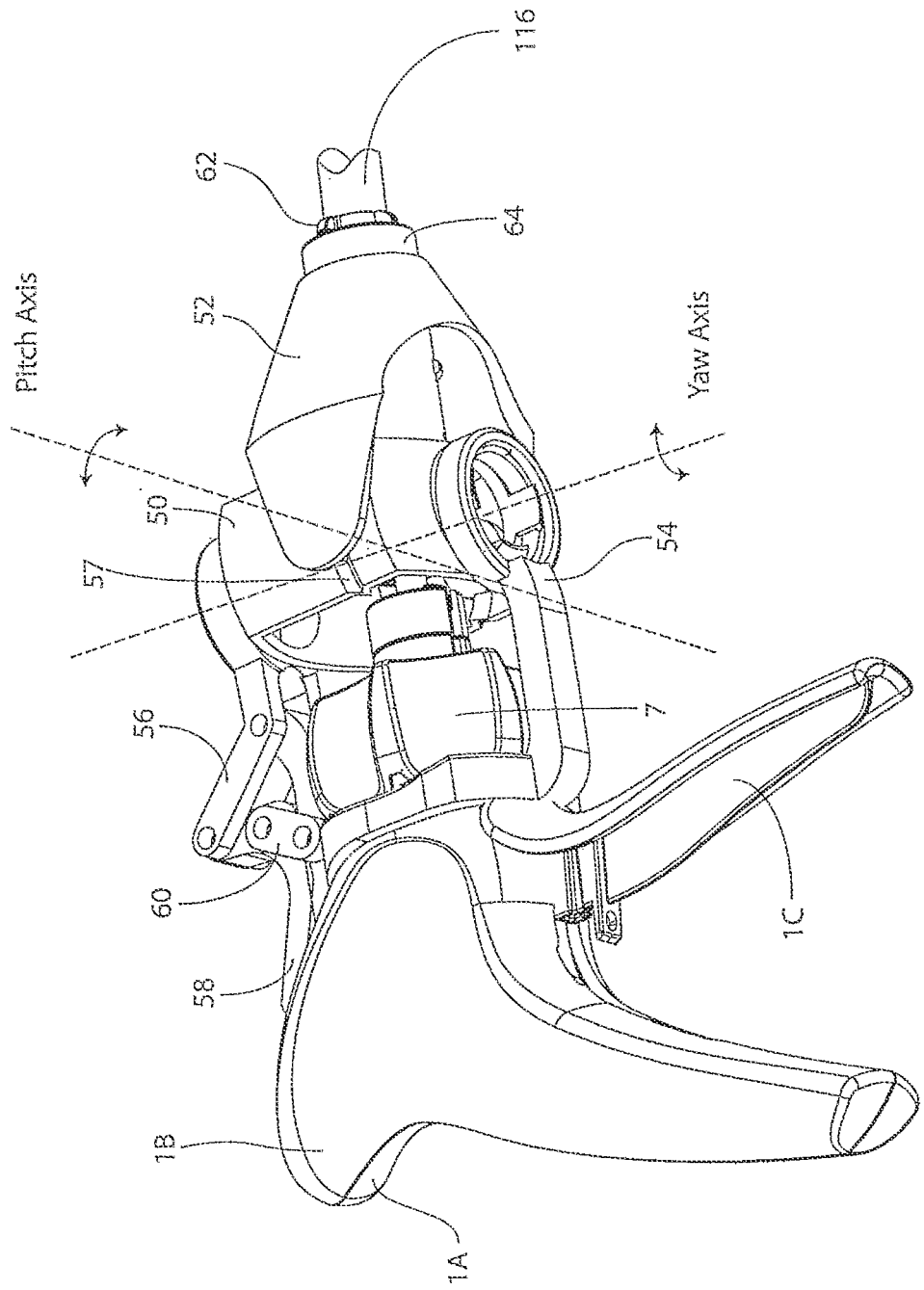
FIG. 17 is a bottom perspective view of the tool of FIG. 15.
Figure 18:
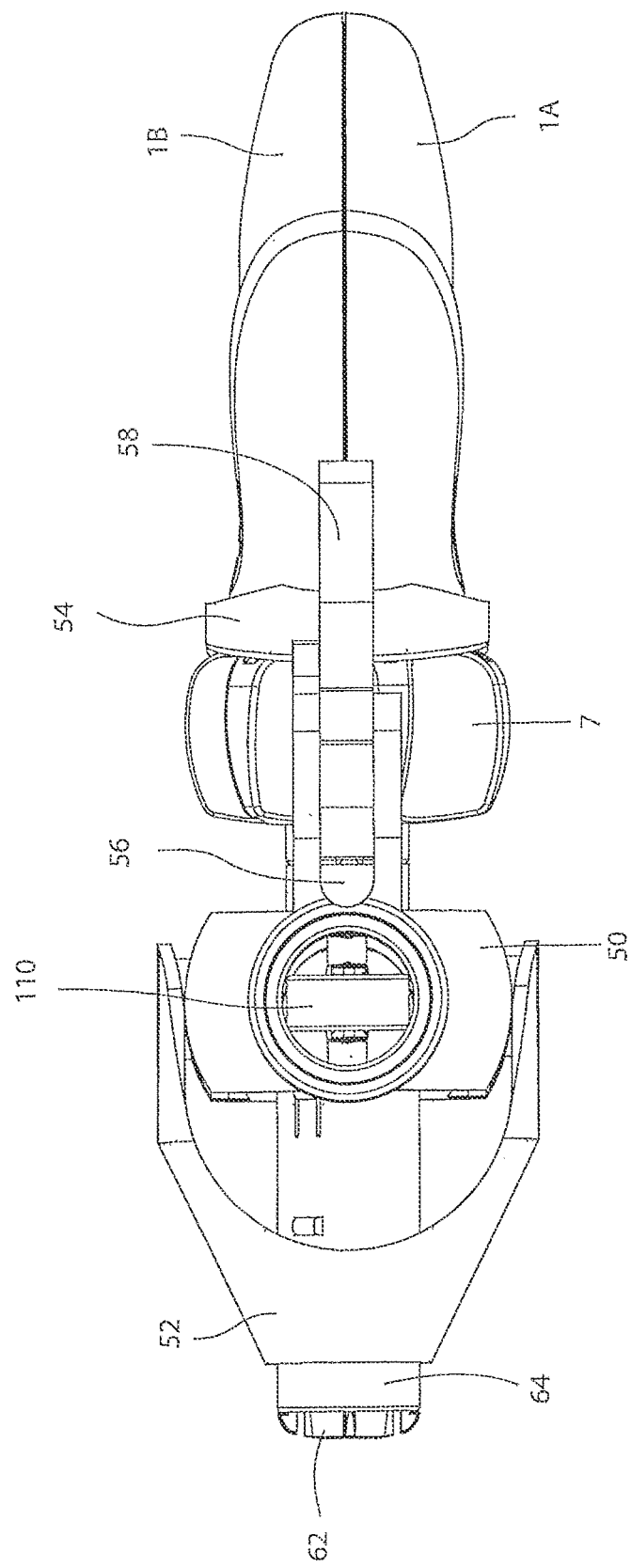
FIG. 18 is a top view of the tool of FIG. 15.
Figure 19:
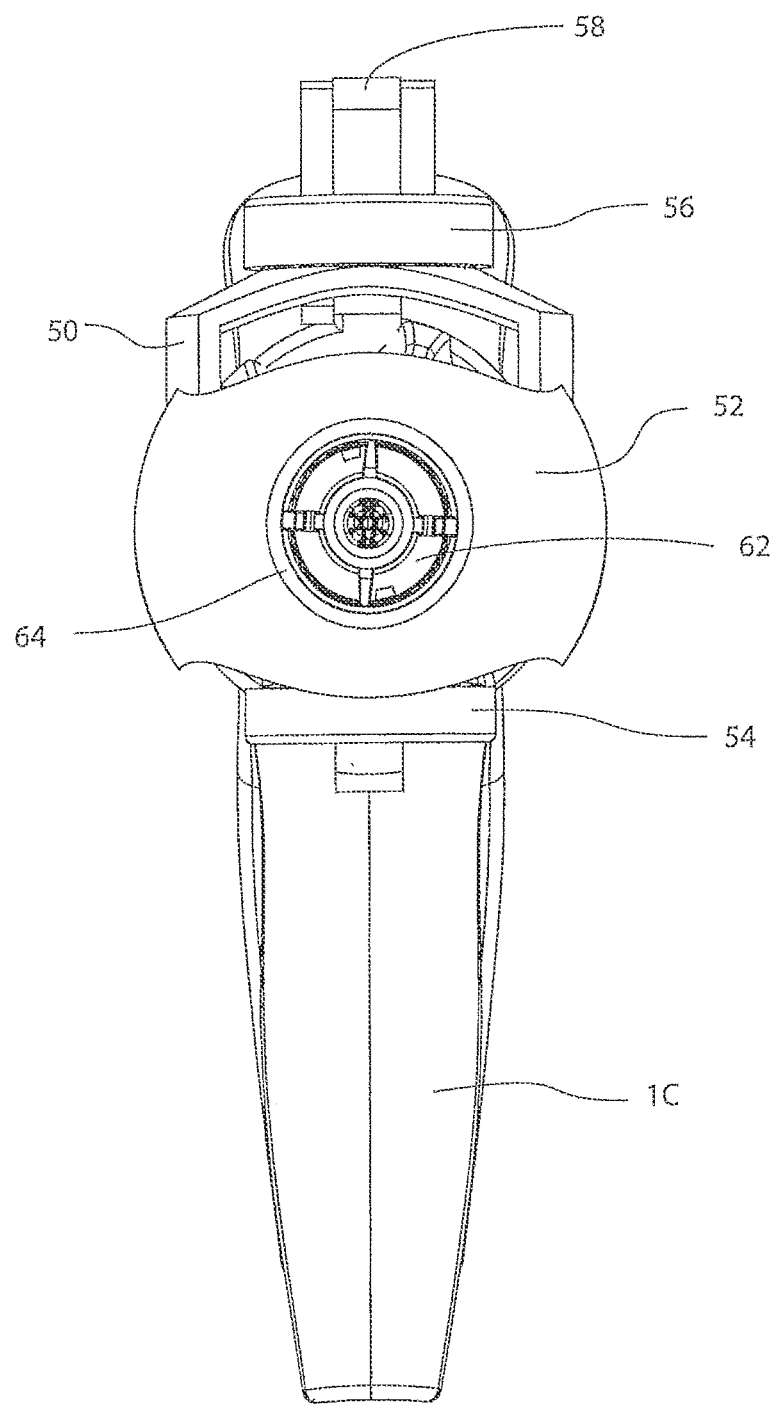
FIG. 19 is a front view of the tool of FIG. 15.
Figure 20:
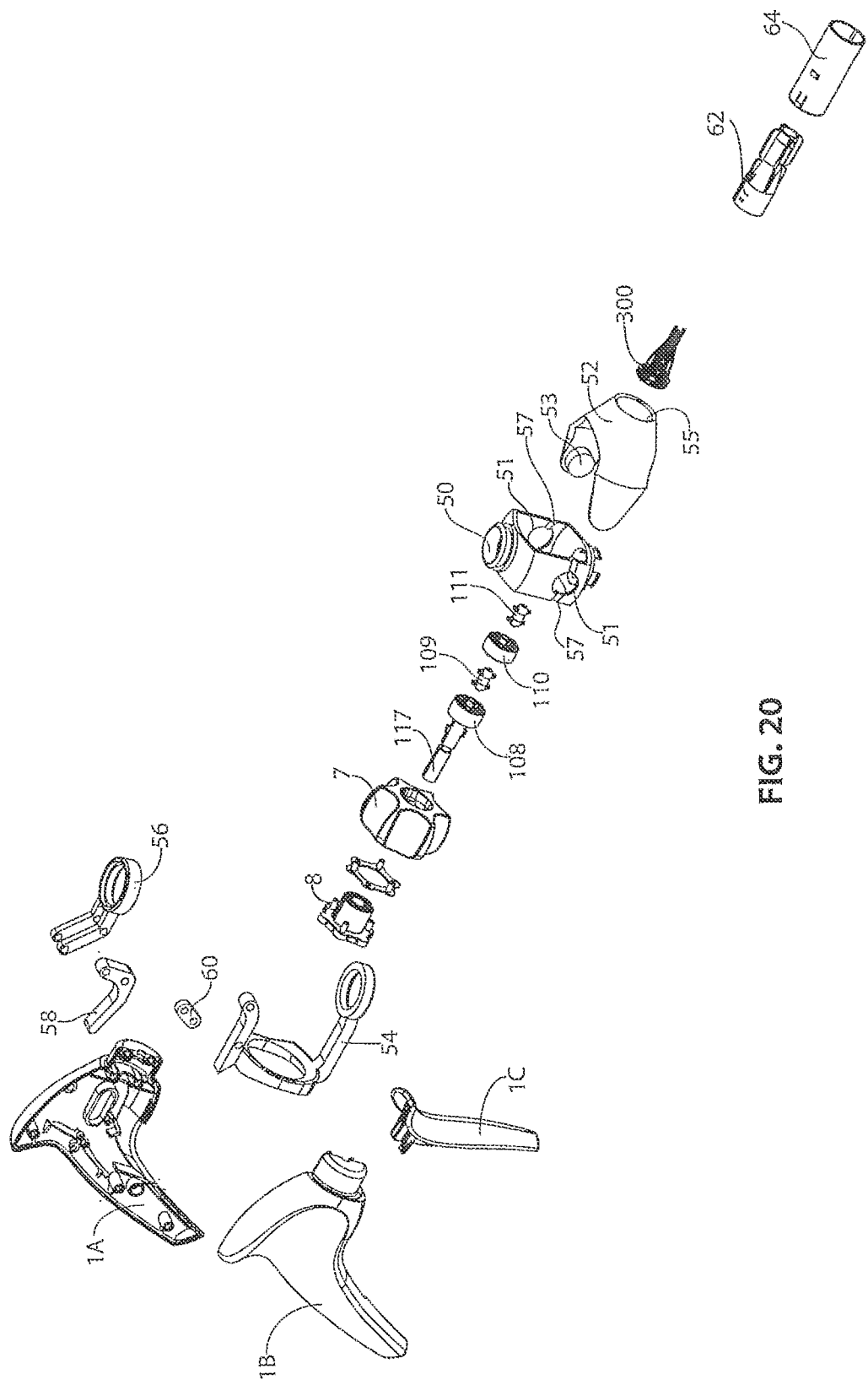
FIG. 20 is a exploded view of the tool of FIG. 15.
Figure 21:
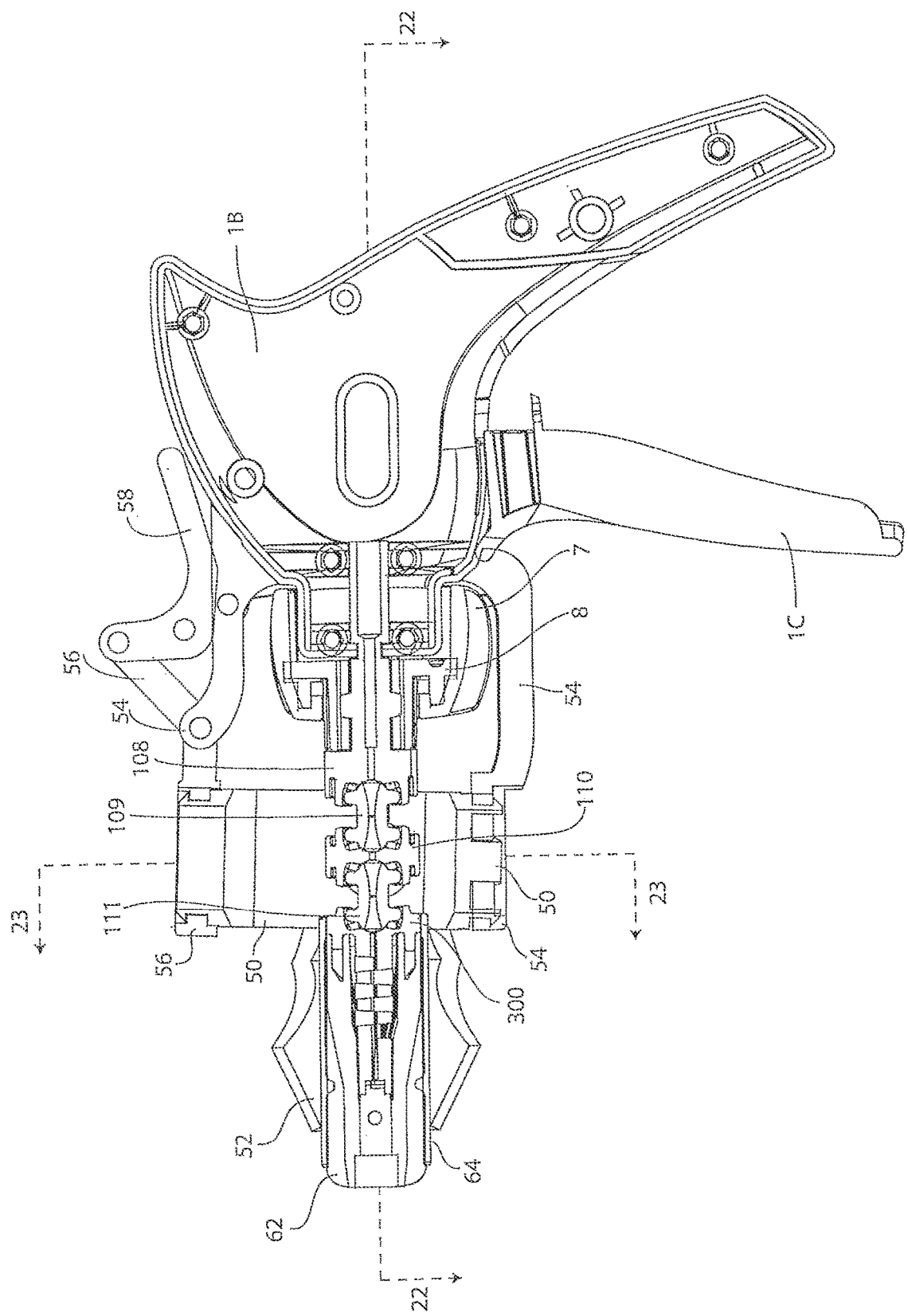
FIG. 21 is a side cross-sectional view taken along the centerline of the tool of FIG. 15.
Figure 22:
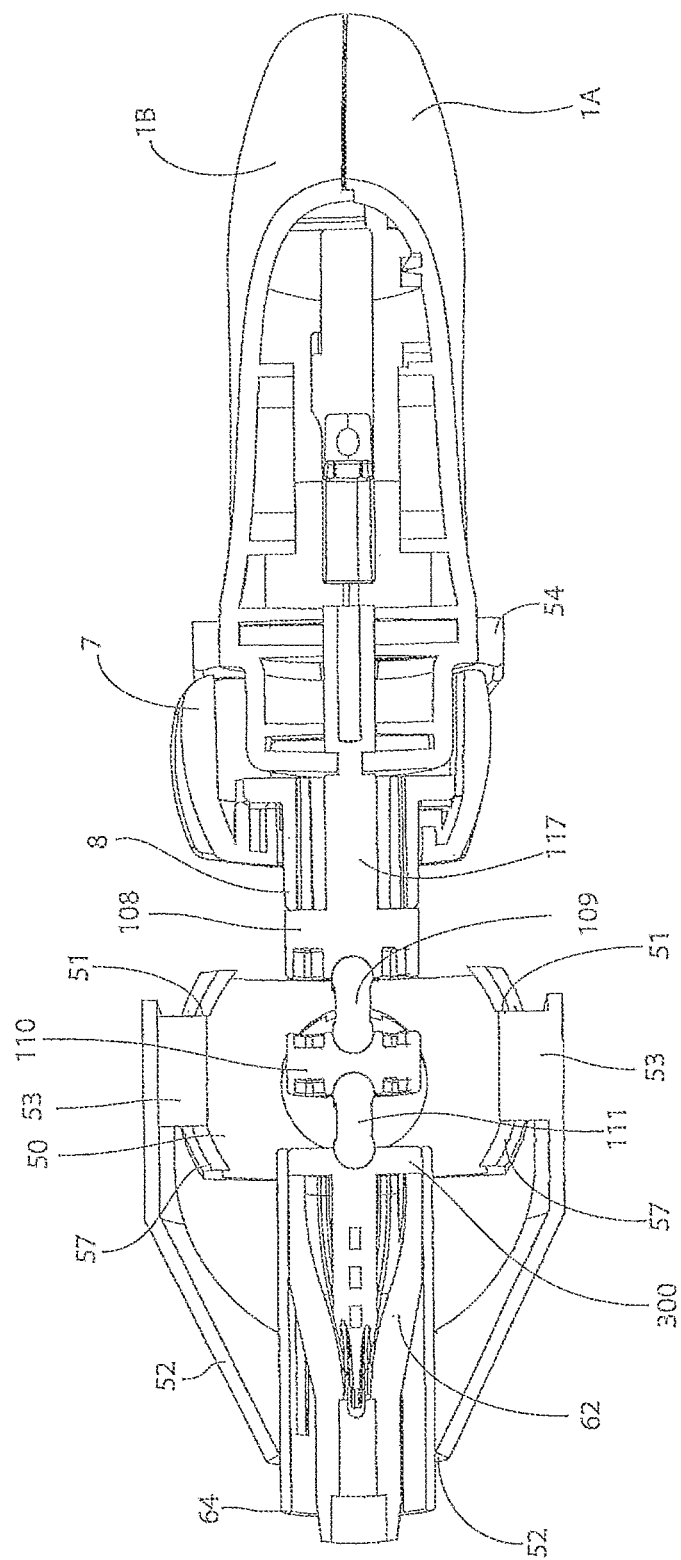
FIG. 22 is a cross-sectional view of the tool of FIG. 15 taken along line 22-22 in FIG. 21.
Figure 23:
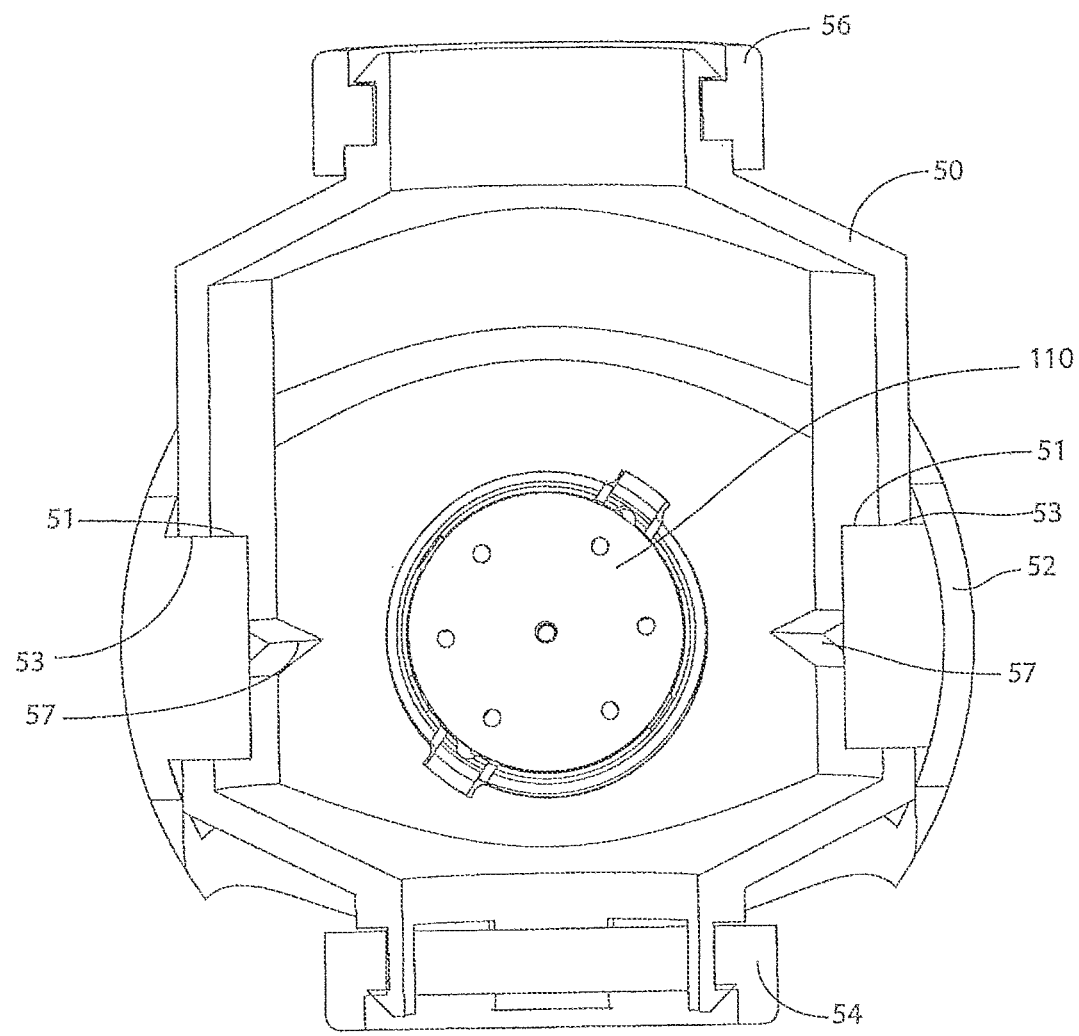
FIG. 23 is a cross-sectional view of the tool of FIG. 15 taken along line 23-23 in FIG. 21.

In the second exemplary embodiment shown in FIGS. 15-23, the instrument includes a base 54 rigidly attached to handle 1. Base 54 includes a lower ring, and pivotably supports an upper ring 56 with a four-bar mechanism. The upper ring is aligned on a common yaw axis with the lower ring of base 54 for pivotably receiving a gimbal 50, as shown in FIG. 17. Gimbal 50 in turn includes two diametrically opposed bores 51 aligned on a pitch axis for pivotably receiving opposing bosses 53 of yoke 32, as depicted in FIG. 20. Yoke 52 includes an axial bore 55 for slidably and rotatably receiving sleeve 64 located on the proximal end of shaft 116. Proximal end cap 300 mates within end cap housing 62 and both serve to guide the tension bearing members as they enter the proximal end of shaft 116. Sleeve 84 fits covers end cap housing 62 and is therefore rigidly secured to the proximal end of shaft 116. Sleeve 64 provides a smooth, cylindrical outer surface that may slide and rotate within axial bore 55 of yoke 52. This arrangement allows shaft 116 to pivot about the pitch and yaw axes, as shown in FIG. 17, when gimbal 50 and yoke 52 are allowed to freely move. Since there is a close sliding fit between the outer surface of sleeve 64 and axial bore 55 of yoke 52, pivoting movement of shaft 116 relative to handle 1 is prevented when gimbal 50 and yoke 52 are in a locked state, as will be described in more detail below.

When locking lever 58 is in a raised or distal position as indicated by the arrow in FIG. 16, upper ring 56 is slightly raised and shaft 116 is permitted to pivot about the pitch and yaw axes as described above. When locking lever 58 is lowered to a proximal, locked position as shown in FIG. 16, upper ring 56 is biased downwardly toward the lower ring of base 54. In this locked position, gimbal 50 is squeezed between upper ring 56 and lower ring 54 and prevented from pivoting due to friction between gimbal 50 and the rings. Gimbal 50 includes a living hinge 57 around its circumference which traverses the diametrically opposing bores (best seen in FIGS. 20 and 23.) As gimbal 50 is axially compressed, its living hinge causes its diametrically opposing bores 51 to collapse around the bosses 53 of yoke 52. Friction between the bores 51 and the bosses 53 prevents yoke 52 and shaft 116 from pivoting about the pitch axis. Therefore, when locking lever 58 is moved to the locked position, shaft 116 is prevented from articulation about either the pitch or the yaw axis, but may still be rotated about its longitudinal axis by turning knob 7. When locking lever 58 is returned to the unlocked position, shaft 116 may be rotated and/or articulated. As can be seen in FIG. 16, the four-bar mechanism of locking lever 58 may be provided with an "over center" configuration to alternately bias the lever in either the locked or the unlocked position. In alternative embodiments (not shown), a sliding clamp such as lock 3 described in the first embodiment above, or other linkages or mechanisms may be used to bias rings 54 and 56 together.

Figure 24:
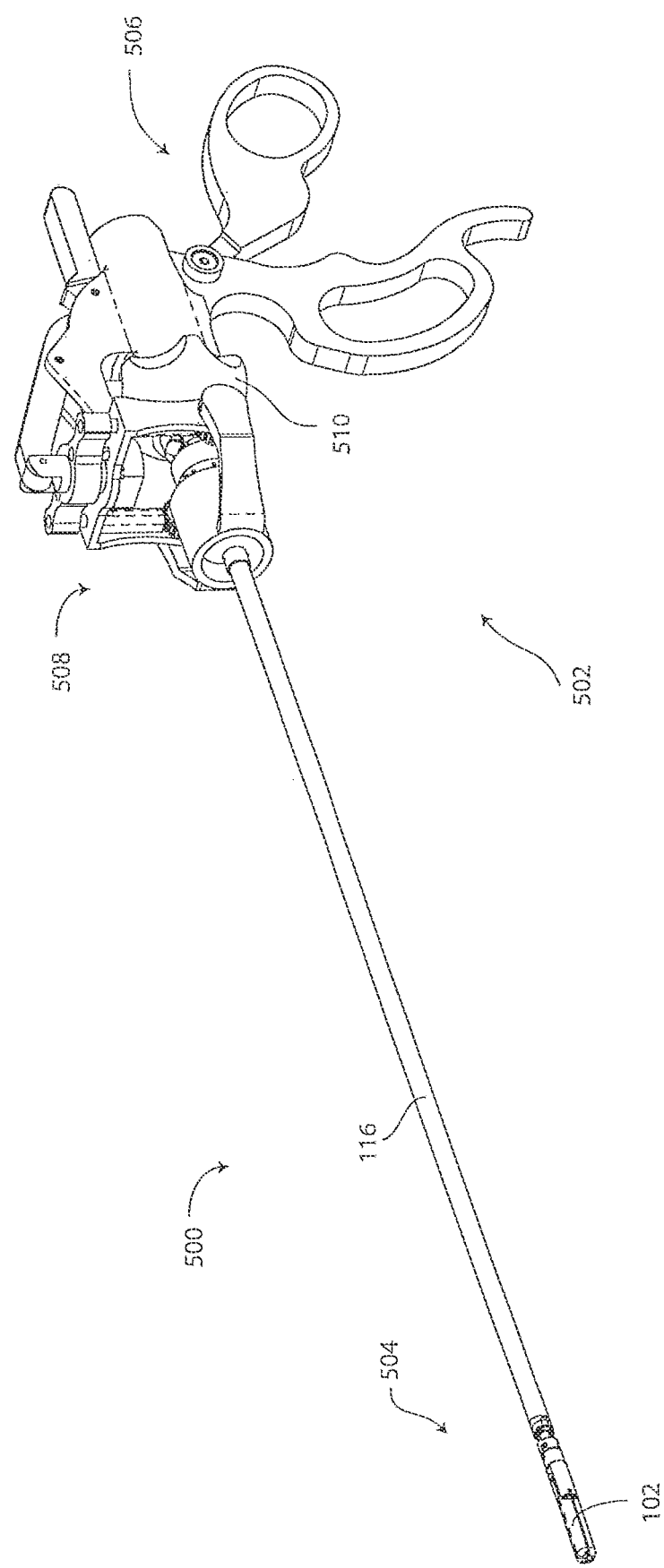
FIG. 24 is a perspective view showing an articulating tool having a third embodiment of an articulation lock.
Figure 25:
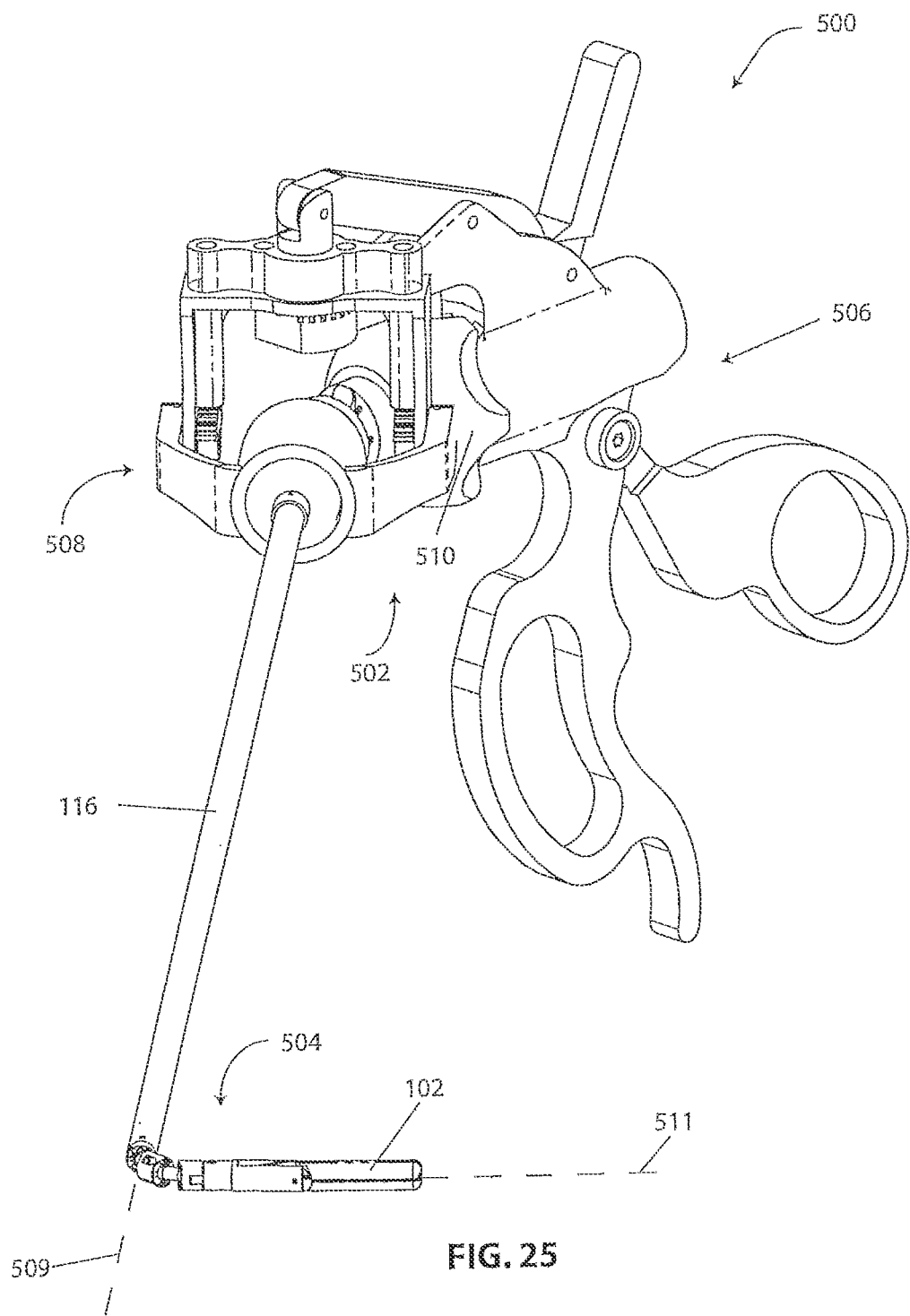
FIG. 25 is a perspective view showing the tool of FIG. 24 in an articulated and locked position.
Figure 26:
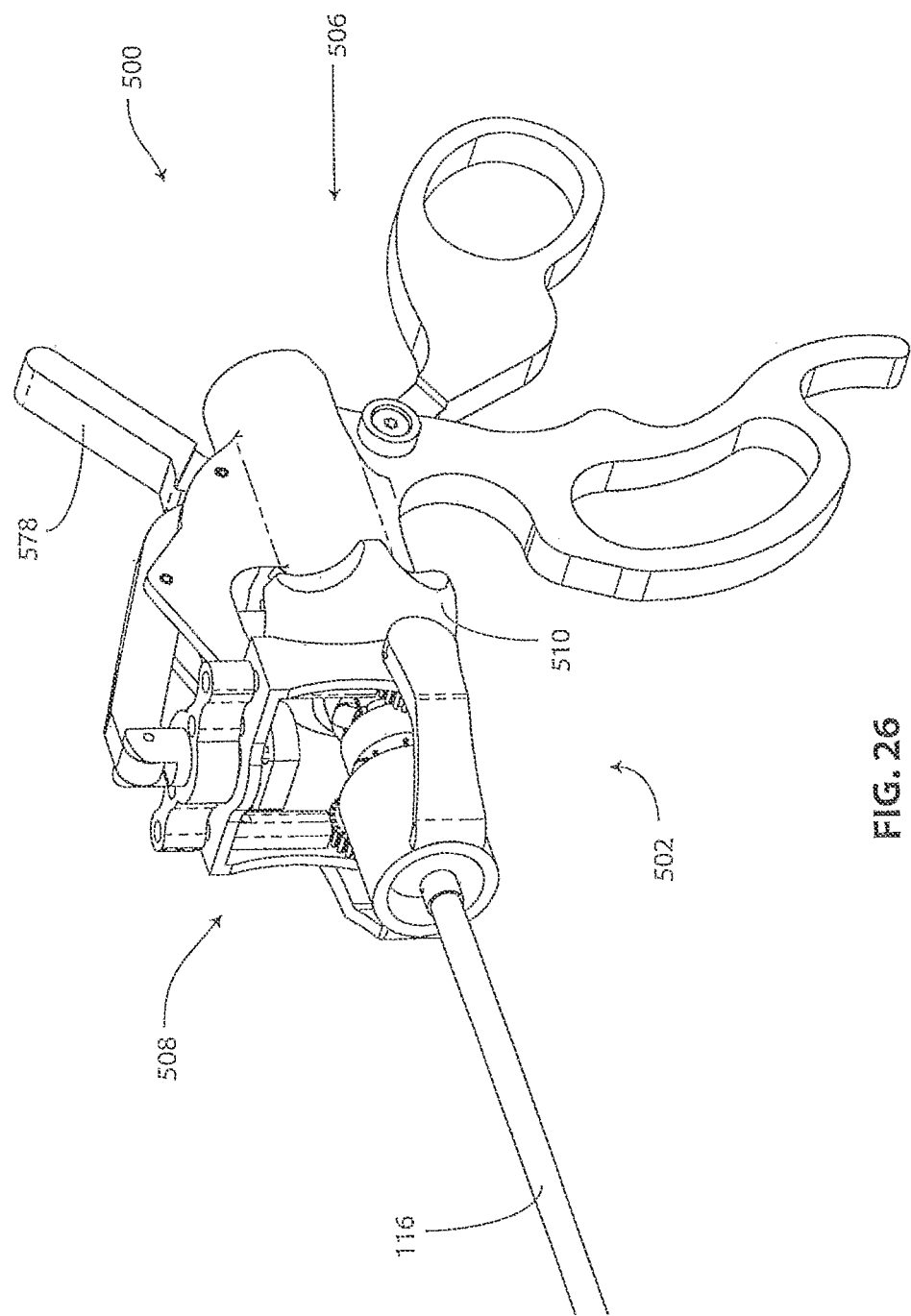
FIG. 26 is an enlarged perspective view showing the proximal end of the tool of FIG. 24 in a centered and locked position.

Referring to FIGS. 24-38, a third articulation lock embodiment is shown and described. Device 500 of this third exemplary embodiment has a proximal portion 502 and a distal portion 504 similar to those of the device shown in FIGS. 1-2 and described above. The proximal portion 502 of the device includes a handle 506 and an articulation lock 508. In an unlocked position, as shown in FIG. 24, shaft 116 and end effector 102 may be articulated relative to handle 506 in a manner similar to that previously described, as depicted in FIG. 25. The articulation lock 508 may then be moved to a locked position, as shown in FIG. 25 for example, in which the proximal end of shaft 116 is held in a fixed orientation relative to handle 506. This in turn locks end effector 102 in a fixed orientation relative to the distal end of shaft 116. In this locked state, the proximal links of the articulation mechanism are prevented from pivoting. Because the proximal and distal links are interconnected by tension members such as cables, this in turn prevents pivoting of the distal links and locks end effector 102 in a fixed orientation relative to the distal end of shaft 116. However, by rotating knob 510, shaft 116 may be caused to rotate about its longitudinal axis 509 even when in a locked position, and end effector 102 is caused to rotate about its own longitudinal axis 511 while being held in a fixed orientation. This feature allows a surgeon to, for example, lock the orientation of an end effector 102 when holding a needle, but rotate end effector 102 about its axis 511 for "throwing a stitch." The orientation of the end effector 102 may be locked and the end effector rotated regardless of whether the axis 511 of end effector 102 is aligned with the axis 509 of shaft 116, as shown in FIG. 24, or is articulated to be at an angle to the shaft, as shown in FIG. 25.

Figure 27:
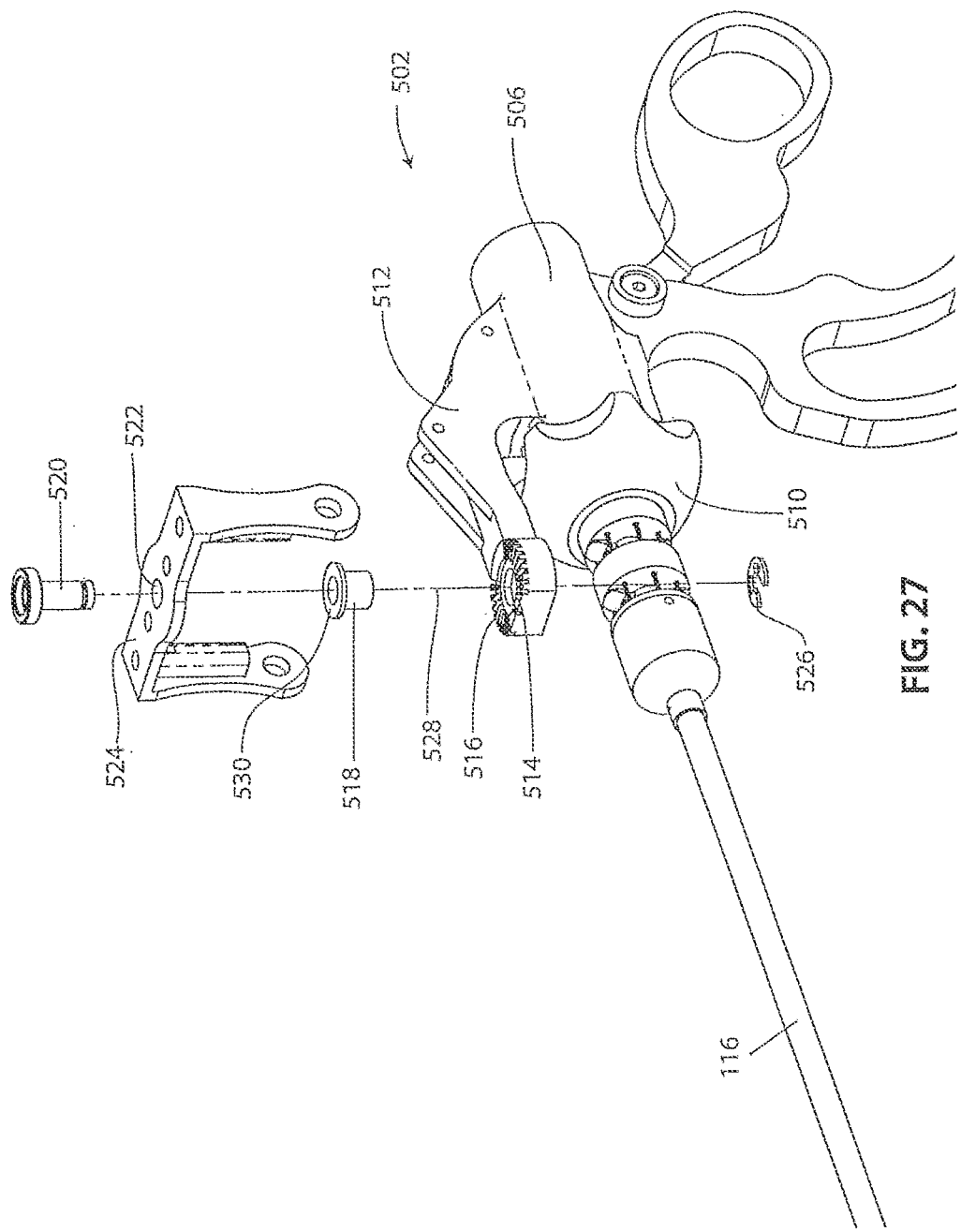
FIG. 27 is an exploded view showing the proximal yoke of the tool of FIG. 24.
Figure 28:
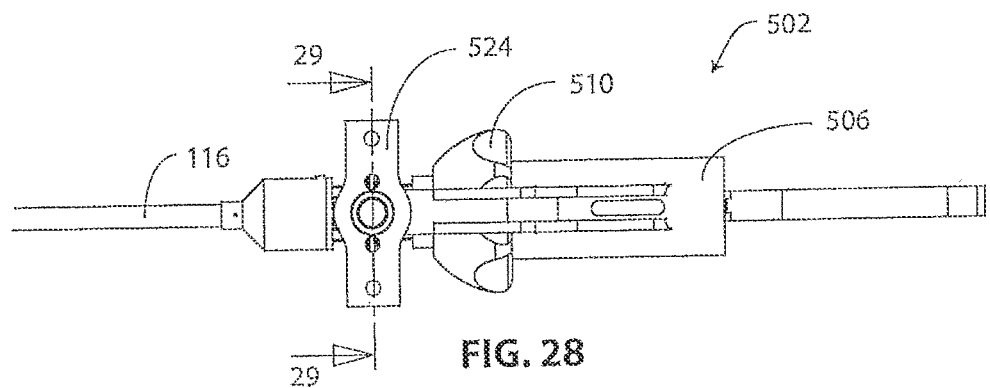
FIG. 28 is a top view showing the tool of FIG. 24.
Figure 29:
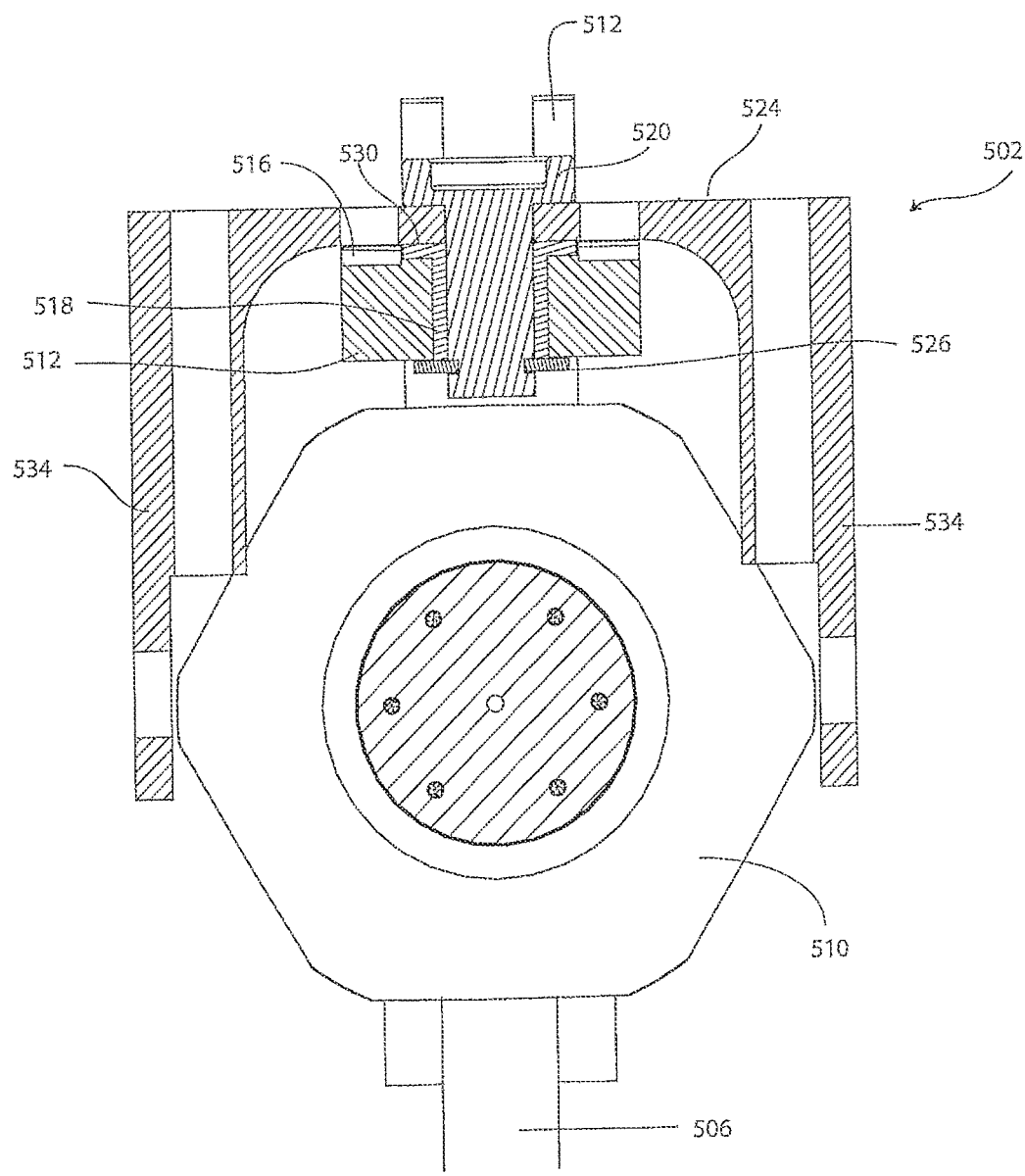
FIG. 29 is a cross-sectional view of the tool of FIG. 24 taken along line 29-29 in FIG. 28.

Starting first with reference to FIGS. 27-29, the construction of the articulation lock 508 of this third exemplary embodiment will be described. Instrument handle 506 includes on a top portion a distally extending support arm 512. Support arm 512 can be an integral part of handle 506 or be a separate component. The distal end of support arm 512 may be provided with a central bore 514, and radially extending gear teeth 516 on its upper surface, as best seen in FIG. 27. Flange bushing 518 is received within central bore 514 of arm 512. Yoke bearing race 520 passes through a central aperture 522 in proximal yoke 524, and passes through flange bushing 518. Proximal yoke 524 is retained on support arm 512 by an E-clip 526 which engages a circumferential slot around the lower end of race 520. In this manner, yoke 524 rotates with respect to arm 512 about a vertical yaw axis 528 as race 520 rotates within bushing 518, and the bottom surface of yoke 524 rides on thrust bearing surface 530 of bushing 518.

Figure 30:
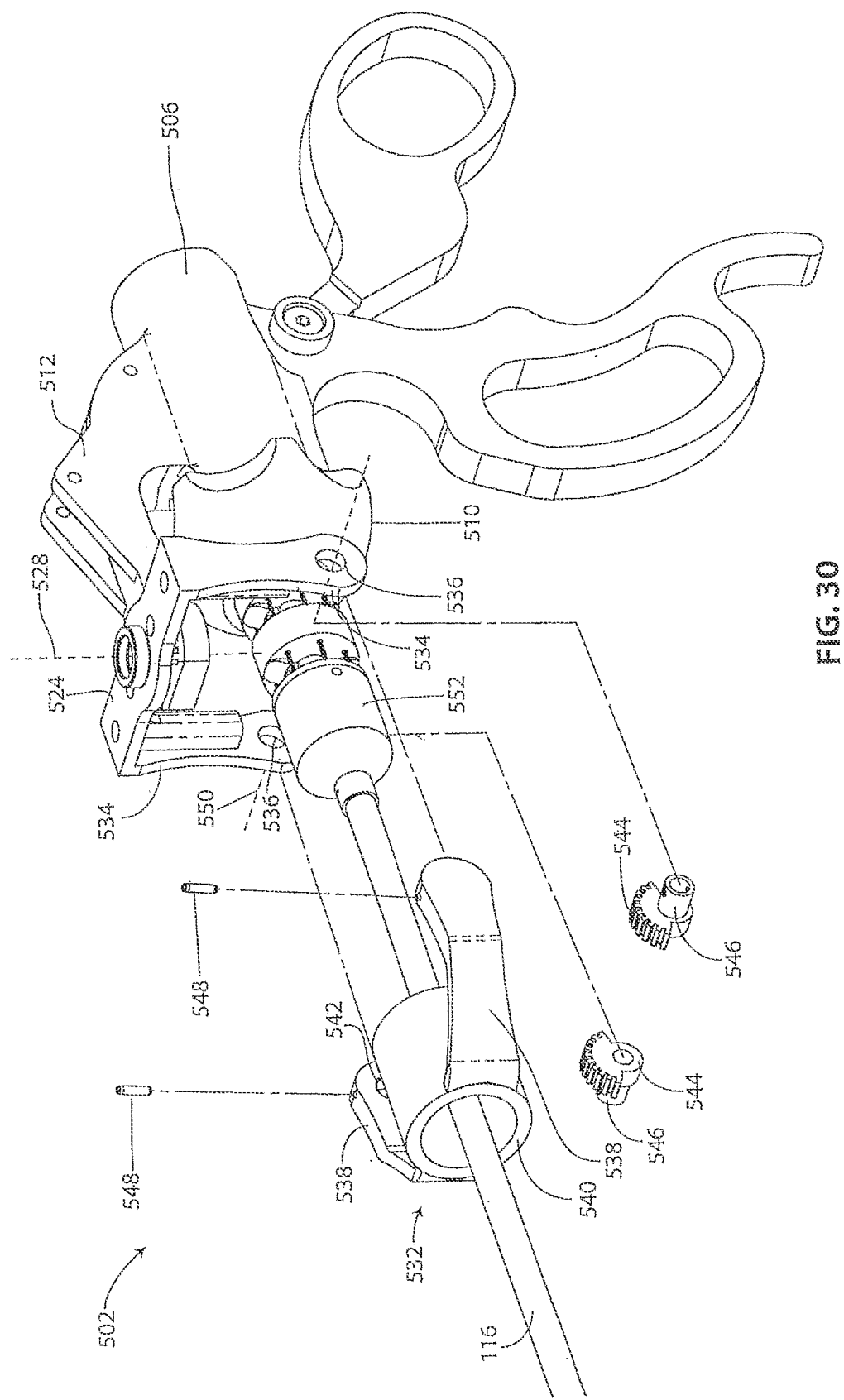
FIG. 30 is an exploded view showing the distal yoke of the tool of FIG. 24.

Referring now to FIG. 30, the assembly of distal yoke 532 with proximal yoke 524 is shown. Proximal yoke 524 is provided with two downwardly depending arms 534 at its lateral extremes. The lower end of each proximal yoke arm 534 is provided with a through hole 536. Similarly, distal yoke 532 is provided with two proximally projecting arms 538 rigidly coupled to a central sleeve 540. The proximal end (relative to the entire instrument 500) of each distal yoke arm 538 is provided with an inwardly facing blind hole 542. Distal yoke 532 is sized such that its arms 538 fit over the arms 534 of proximal yoke 524, allowing holes 542 of arms 538 to align with holes 536 of arms 534. Two gear segments 544 are each provided with an outwardly facing boss 546. Each boss fits through a pair of aligning holes 542, 536 and is rigidly attached to one of the distal yoke arms 538 with a pin 548, by a press fit, or other suitable attachment means. With this arrangement, bosses 546 pivot within holes 536 of proximal yoke 524, thereby allowing distal yoke 532 to rotate about a pitch axis 550 that passes through holes 536. As distal yoke arms 538 rotate on the outside of proximal yoke arms 534, gear segments 544 rotate on the inside of arms 534.

Sleeve 540 of distal yoke 532 is designed to slidably mate with drum 552 which is rigidly affixed to the proximal end of instrument shaft 116. In this exemplary embodiment, shaft drum 552 may freely rotate within sleeve 540, and drum 552 may also slide axially relative to sleeve 540. In operation, when instrument handle 506 is articulated with respect to shaft 116, distal yoke sleeve 540 is allowed to follow shaft drum 552 because distal yoke 532 is allowed to pivot relative to proximal yoke 524 about pitch axis 550, and proximal yoke 524 is allowed to pivot relative to handle 506 about yaw axis 528, as previously described. However, when articulation lock 508 is moved to a locked position, as will be described below, the pivoting of both yokes 524 and 532 is prevented. This locks distal yoke sleeve 540 from further movement relative to handle 506, which in turn maintains instrument shaft 116 in a fixed angular orientation relative to handle 506. As previously described, locking the orientation of shaft 116 relative to handle 506 consequently locks the orientation of the proximal link(s) of the instrument. This in turn locks the orientation of the distal link(s) since they are interconnected with the proximal link(s) by tension bearing members such as cables. When the distal link(s) are in a locked orientation, axis 511 of end effector 102 (shown in FIG. 25 is generally locked in a fixed orientation relative to handle 506 as well.

Figure 31:
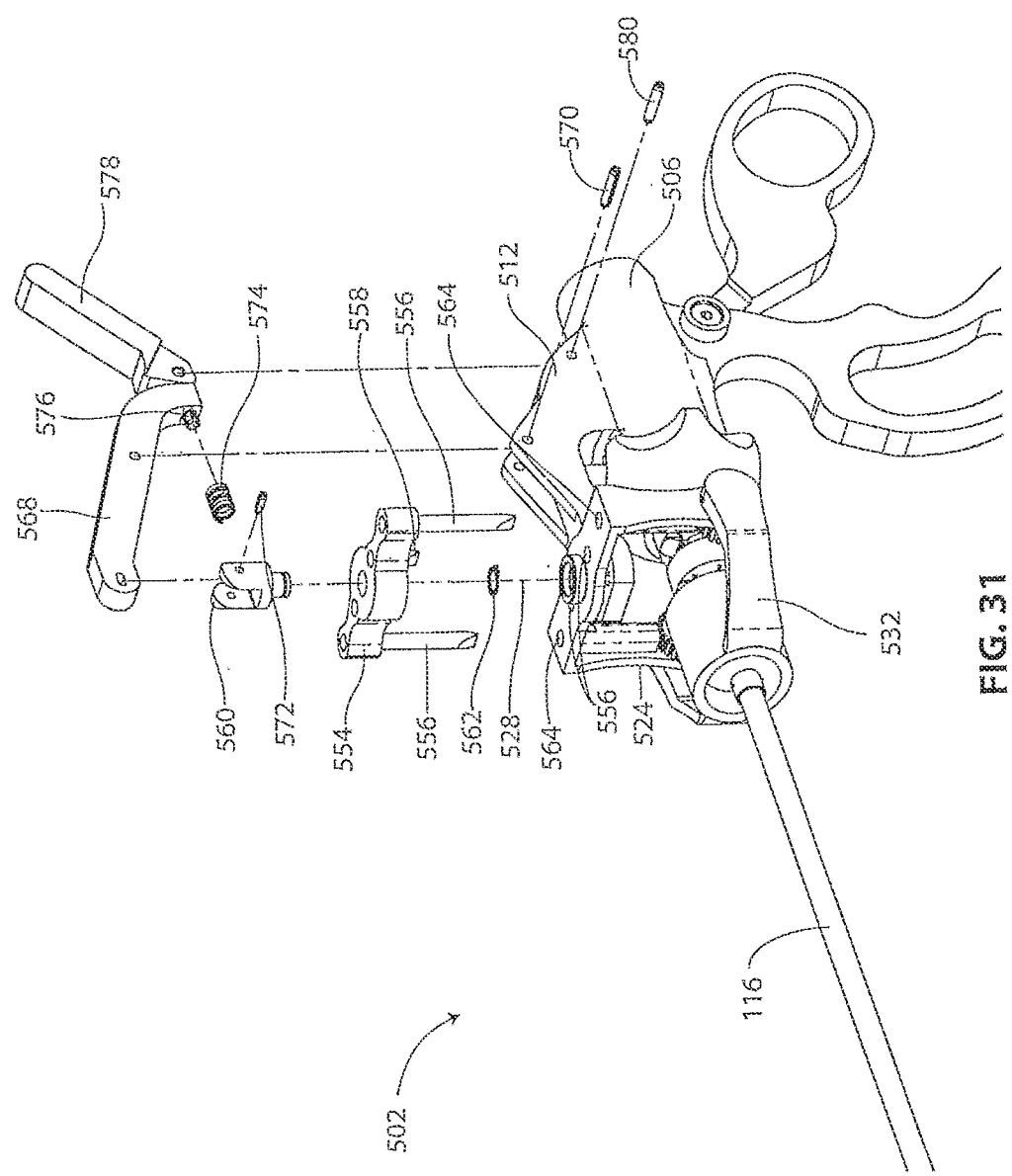
FIG. 31 is an exploded view showing the pin holder and operating levers of the tool of FIG. 24.

Referring to FIG. 31, the assembly of additional locking components will be described. Pin holder 554 includes two downwardly extending long pins 556, which are rigidly attached on opposite sides of pin holder 554. Pin holder also includes two downwardly extending short pins 558 (only one seen in FIG. 31), which are also rigidly attached on opposite sides of pin holder 554, inboard from long pins 556. Pin holder 554 is also provided with a central bore for receiving a downwardly extending boss of clevis 560. The boss of clevis 560 includes a groove for receiving snap ring 562. When assembled, clevis 560 may rotate but not move axially relative to pin holder 554.

The horizontal portion of proximal yoke 524 includes two outer holes 564 for receiving the long pins 556 and two inner holes 566 for receiving the short pins 558. When assembled, pin holder 554 rotates along with proximal yoke 524 about the vertical yaw axis 528. Pin holder 554, along with pins 556 and 558, may also be moved vertically relative to proximal yoke 524 between an upper unlocked position and a lower locked position, as will be described in more detail below.

Lever 568 is pivotably mounted to support arm 512 of handle 506 by pin 570. Lever 568 is also pivotably coupled to clevis 560 by pin 572. As lever 568 pivots about pin 570, lever 568 drives pin holder 554 vertically with clevis 560. Spring 574 is mounted on boss 576 of lever 568 to urge lever 568 toward a locked position, as will be described in more detail below. Locking lever 578 is pivotably mounted to support arm 512 of handle 506 by pin 580 to drive lever 568.

Figure 32:
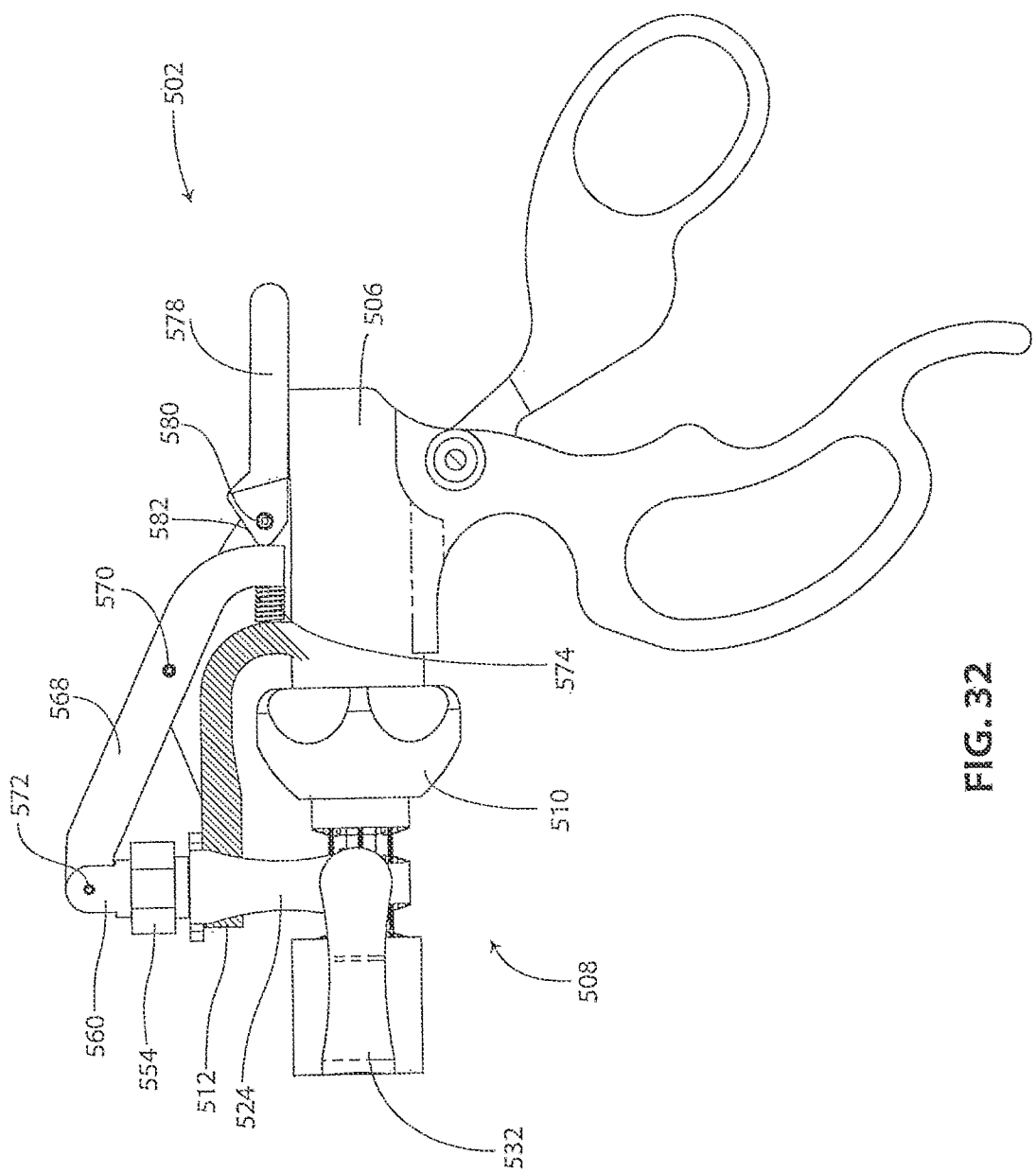
FIG. 32 is a broken away side view showing the articulation lock of the tool of FIG. 24 in an unlocked state.
Figure 33:
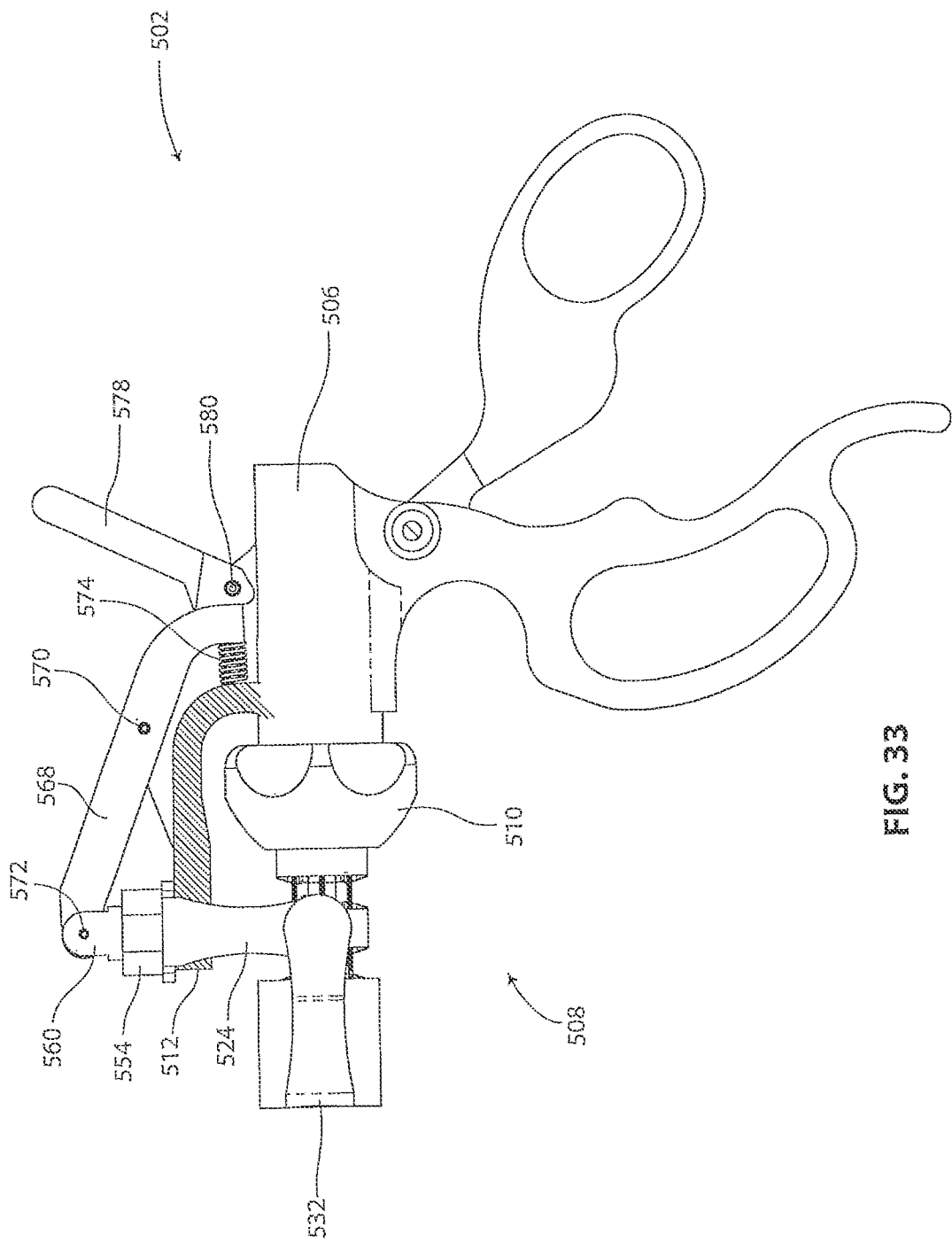
FIG. 33 is a broken away side view showing the articulation lock of the tool of FIG. 24 in a locked state.

Referring to FIGS. 32 and 33, details of the operation of levers 568 and 578 are shown. FIG. 32 shows articulation lock mechanism 508 in the unlocked state and FIG. 33 shows it in the locked state. First, instrument 500 is articulated into the desired position by pivoting handle 506 relative to shaft 116, as shown in FIG. 25 for example. Articulation lock mechanism 508 is then operated by moving locking lever 578 between a lower unlocked position (FIG. 32) and an upper locked position (FIG. 33). This can be accomplished by the surgeon by using the thumb or the index finger of the hand that is holding handle 506. Alternatively, the surgeon may operate looking lever 578 with the opposite hand. When locking lever 578 is pivoted upwardly, a cam surface 582 on locking lever 578 allows spring 574 to urge the proximal end of lever 568 in a proximal direction. This in turn causes lever 568 to pivot counter-clockwise about pin 570, driving clevis 560 and pin holder 554 downward to the position shown in FIG. 33. In this embodiment, cam surface 582 is shaped such that when locking lever 578 is moved a relatively small distance towards the locked position, spring 574 urges lever 568 against cam surface 582 and causes locking lever 578 to snap the rest of the way to the locked position and holds it there. Therefore, in this exemplary embodiment, it takes more force to compress spring 574 in moving locking lever 578 to the lower, unlocked position than it does to move locking lever 578 to the upper, locked position. In alternative embodiments (not shown), the contact point between levers 578 and 568 may be modified such that locking lever 578 is pushed upward (i.e. rotated counter clockwise) to unlock. In this way, 578 would be up in the unlocked position and down in the unlocked position. Other mechanisms, buttons or sliders that are well known in the art may be used to actuate pin holder 554 and pins 556 and 558 up and down.

Referring to FIGS. 35 and 36 (both cross sections taken along line 35-35 in FIG. 34), details of operation of a second articulation lock portion 584 of articulation lock 505 are shown. (The first articulation lock portion will be later described.) FIG. 35 shows second articulation lock 584 in an unlocked position, and FIG. 36 shows it in a locked position. In FIG. 35 it can be seen that when pin holder 554 is moved to its raised, unlocked position by operation of locking lever 578, the beveled lower ends of long pins 556 are disengaged from the teeth of gear segment 554 (only one of each are seen in FIGS. 35 and 36), thereby permitting instrument shaft 116 to pivot with distal yoke 532 about pitch axis 550. Conversely, it can been seen in FIG. 36 that when pin holder 554 is moved to its lowered, locked position, the beveled lower ends of long pins 556 are engaged with the teeth of gear segments 554, thereby preventing shaft 116 from pivoting about pitch axis 550. Again, motion of shaft 116 is prevented because gear segments 554 are rigidly congested to distal yoke 532, which has a sleeve 540 that constrains pivoting movement of shaft drum 552, shown in FIG. 30.

In alternative embodiments (not shown), locking of the distal yoke can be accomplished in a variety of other ways. For example, a downwardly facing concave gear segment may be placed on the lower end of long pin 556 and an upwardly facing beveled pin may be coupled to distal yoke for engaging with the gear segment when it is lowered by long pin 556. In another embodiment, the long pin may have a smaller diameter and alternately engage with a series of holes formed in a drum located on pitch axis 550 in place of gear segments 554. In yet another embodiment, a brake pad or compressible elastomer may be attached to the lower end of long pin 556 for engaging with a drum located on pitch axis 550 in place of gear segments 554. In some of these alternative embodiments, there may be discrete detent or locking positions, while in other embodiments the availability of various locking positions may be finer or infinitely variable.

Figure 38:
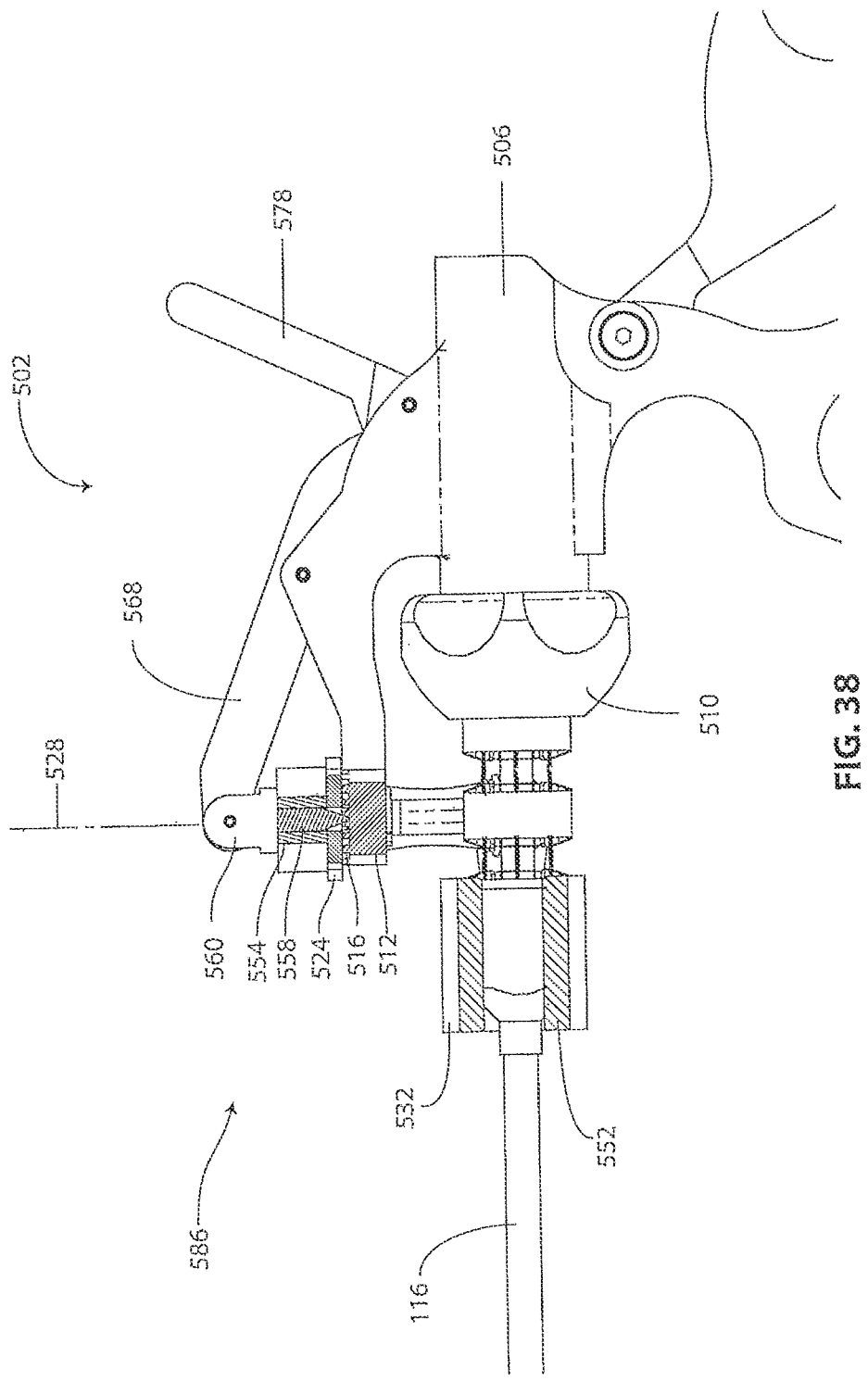
FIG. 38 is a cross-sectional view of the tool of FIG. 24 taken along line 37-37 in FIG. 34 showing a first articulation lock in an unlocked state.

Referring to FIGS. 37 and 38 (both cross sections taken along line 37-37 in FIG. 34), details of operation of a first articulation lock portion 586 of articulation lock 508 are shown. FIG. 37 shows first articulation lock 586 in an unlocked position and FIG. 38 shows it in a locked position. In FIG. 37 it can be seen that when pin holder 554 is moved to its raised, unlocked position by operation of locking lever 578, the beveled lower ends of short pins 558 (only one pin 558 seen in FIGS. 37 and 38) are disengaged from the gear teeth 516 formed on the distal end of support arm 512, thereby permitting instrument shaft 116 to pivot with proximal yoke 524 about yaw axis 528. Conversely, it can been seen in FIG. 38 that when pin holder 554 is moved to its lowered, locked position, the beveled lower ends of short pins 558 are engaged with gear teeth 516, thereby preventing shaft 116 from pivoting about yaw axis 528. Motion of shaft 116 about yaw axis 528 is prevented because short pins 558 are slidably coupled to proximal yoke 524, and when short pins 558 engage with gear teeth 516 they prevent proximal yoke 524 from moving relative to handle 506. Proximal yoke 524 in turn supports distal yoke 532, which has sleeve 540 that constrains pivoting movement of shaft drum 552, shown in FIG. 30.

In alternative embodiments (not shown), locking of the proximal yoke can be accomplished in a variety of other ways. For example, circular pins for alternately engaging in a series of mating holes, or other detent mechanisms may be provided instead of short pins 558 and mating gear teeth 516. Alternatively, clutch plates and/or compressed elastomers such as o-rings may instead be used for finer or infinite rotational position adjustment.

As described above, first articulation lock 586 prevents pivoting motion of shaft 116 relative to handle 506 about yaw axis 528 when engaged. Similarly, second articulation lock 584 prevents pivoting motion of shaft 116 relative to handle 506 about a pitch axis 550 when engaged. Again it is noted that shaft 116 and end effector 102 may be rotated about their axes (509 and 511, respectively) when, the articulation locks are engaged or disengaged. Articulation lock 508 of exemplary instrument 500 engages and disengages first articulation lock 586 and second articulation lock 584 together and at substantially the same time. In other embodiments (not shown), a single actuator may also actuate both the first and second articulation locks, but may do so in a staggered fashion such that one of the articulation locks is actuated first and the other articulation lock is actuated second. In some of these embodiments, the instrument may be locked from pivoting about one axis while permitting articulation about a second axis which may or may not be later locked. In other embodiments, separate actuators may be provided for engaging the first and second articulation locks. Additionally, lockable axes other than the exemplary pitch and yaw axes described above may be used to lock the pivoting movement of an articulating instrument.

Referring to FIGS. 39-44, the proximal portion of a fourth exemplary embodiment is shown and described. In some of these figures, bellows 801 and guy wires 809, which both normally span between base 802 and tie down 804, are omitted for clarity. Bellows 801 are configured to cover the guy wires 809 by spanning from groove 802C to groove 804B. In some figures, the left or right half of base 802 is also omitted for clarity. The device of this embodiment may have a distal portion (not shown) similar to that shown in FIGS. 1-2 and described above.

The proximal portion of the device includes an articulation lock. In an unlocked position, shaft 116 and end effector 102 (both shown in FIGS. 1-2) may be articulated relative to handle 808 in a manner similar to that previously described. The articulation lock may then be moved to a locked position in which the proximal end of shaft 116 is held in a feed orientation relative to handle 808. In this locked state, the proximal links of the articulation mechanism are prevented from pivoting. Because the proximal and distal links are interconnected by tension members such as cables, this in turn prevents pivoting of the distal links and locks end effector 102 in a fixed orientation relative to the distal end of shaft 116. However, by rotating knob 806, shaft 116 may be caused to rotate about its longitudinal axis even when in a locked position, and end effector 102 is caused to rotate about its own longitudinal axis while being held in a fixed orientation. This feature allows a surgeon to, for example, lock the orientation of an end effector 102 when holding a needle, but rotate end effector 102 about its axis for "throwing a stitch." The orientation of the end effector 102 may be locked and the end effector rotated regardless of whether the axis of the end effector 102 is aligned with the axis of the shaft 116 or is articulated to be at an angle to the shaft.

Figure 39:
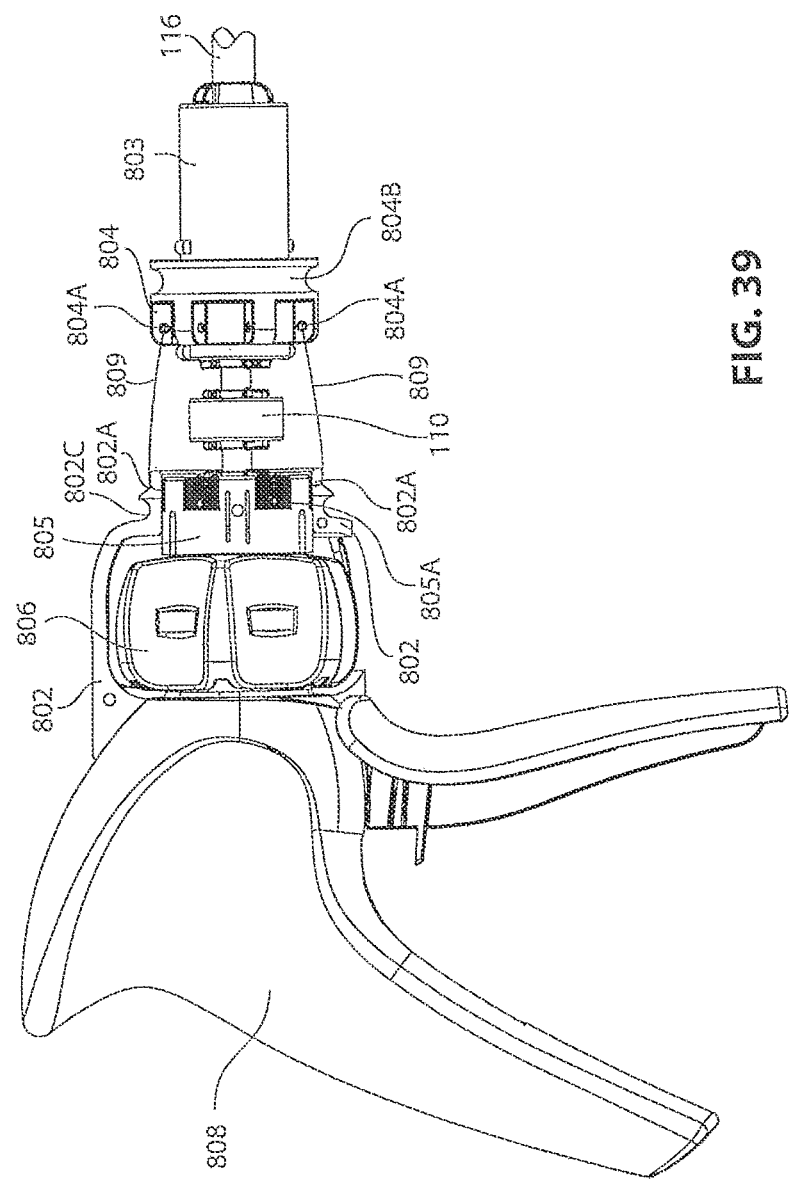
FIG. 39 is a right side view of a fourth embodiment of an articulation lock shown on the proximal end of an articulating tool.
Figure 40:
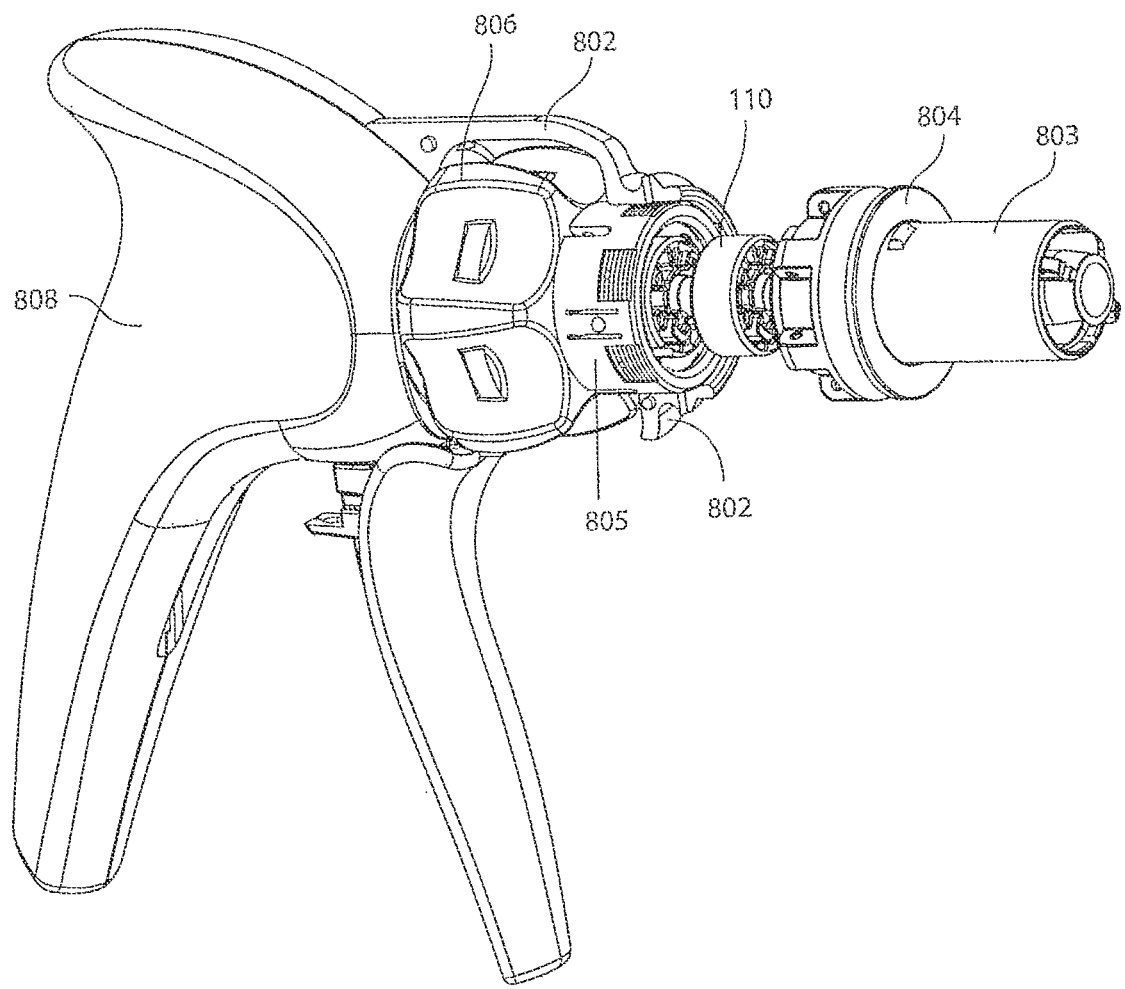
FIG. 40 is a right side perspective view of the tool of FIG. 39.
Figure 41:
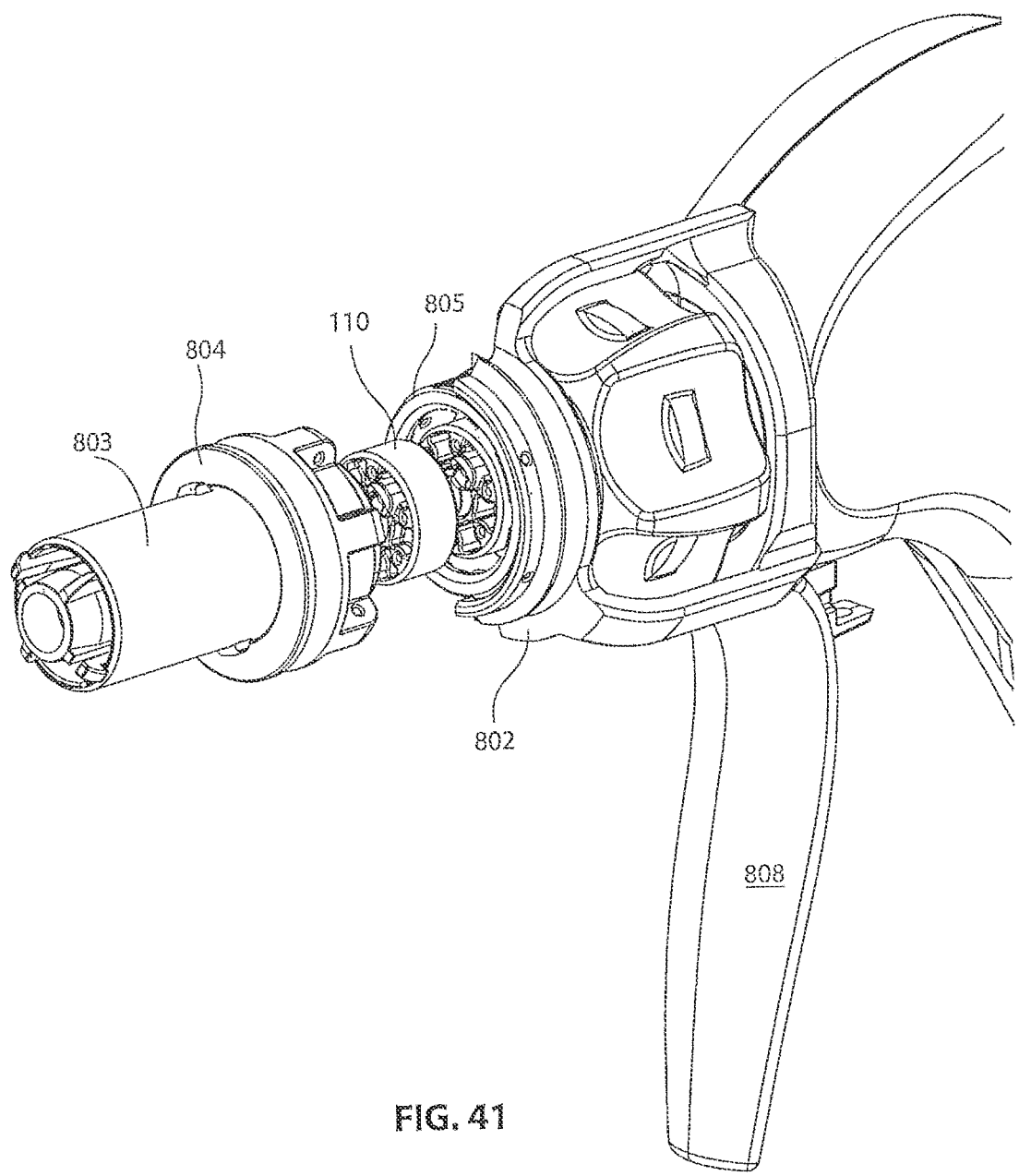
FIG. 41 is an enlarged left side perspective view of the tool of FIG. 39.
Figure 42:
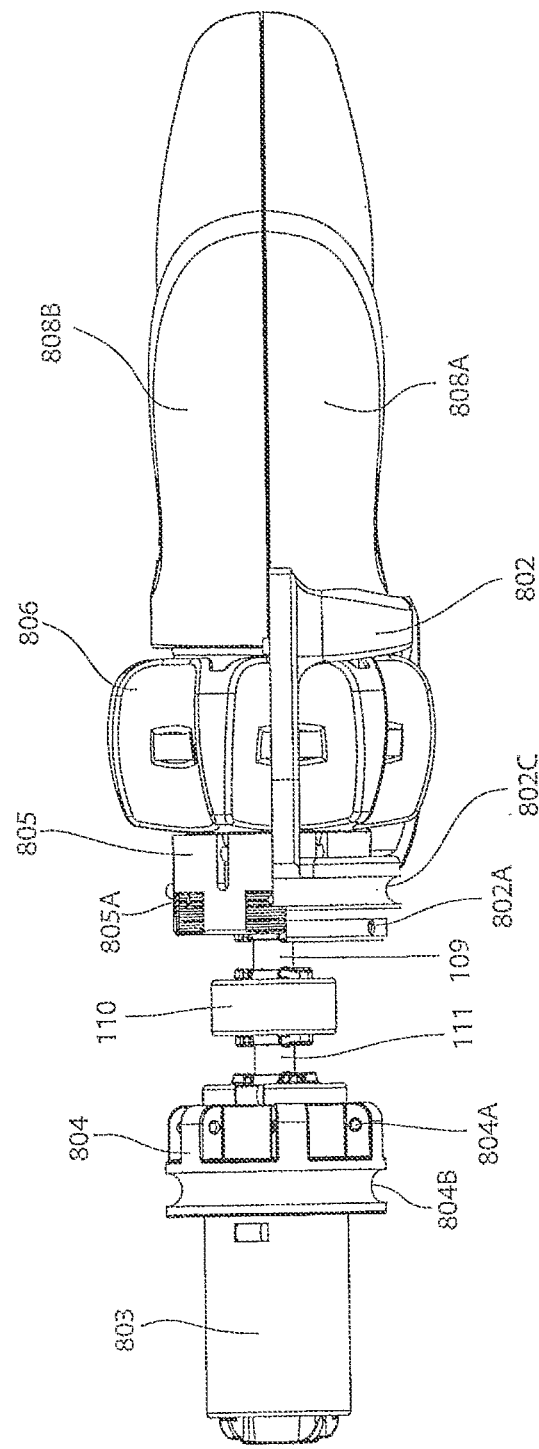
FIG. 42 is a top view of the tool of FIG. 39.
Figure 43:
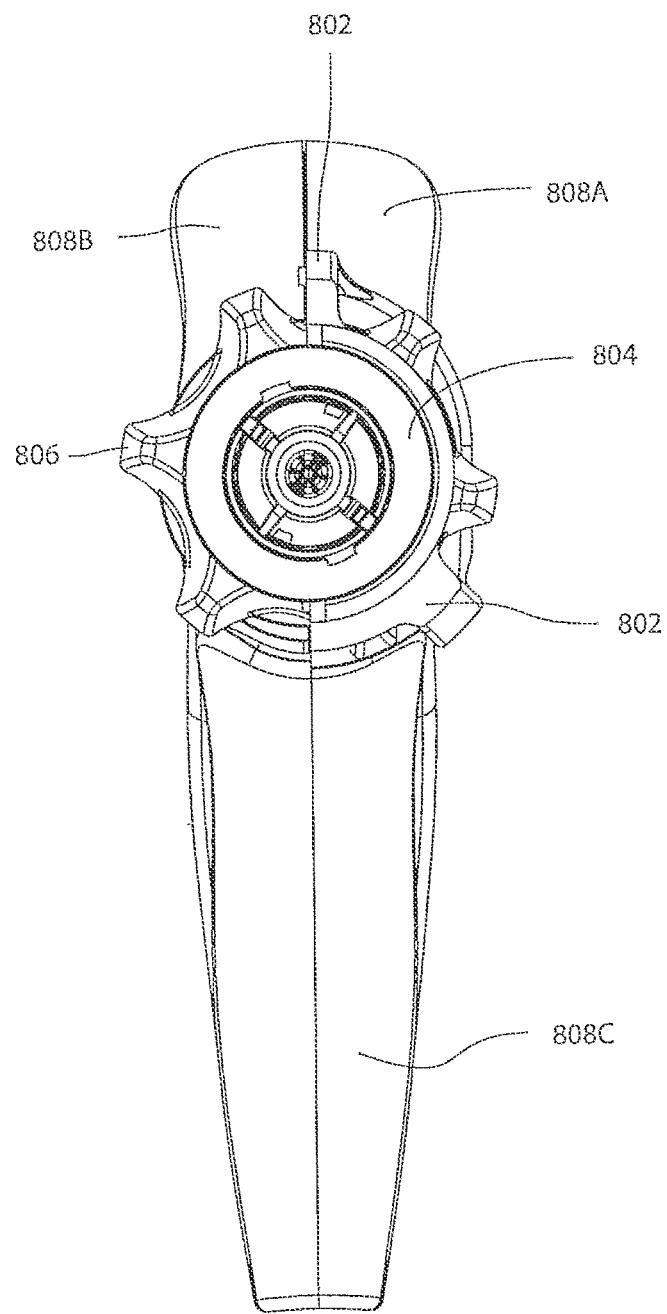
FIG. 43 is a front view of the tool of FIG. 39.
Figure 44:
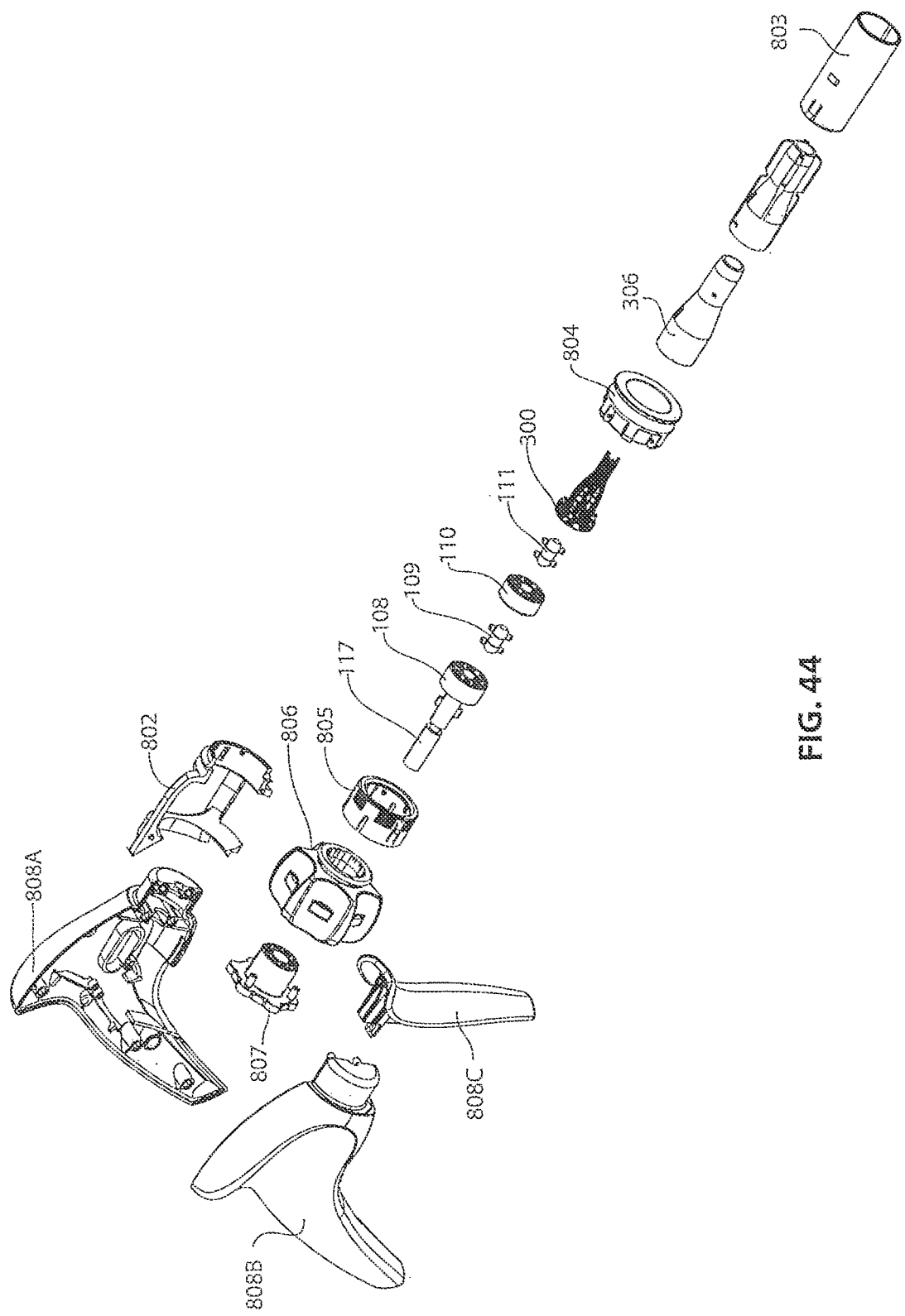
FIG. 44 is an exploded view of the tool of FIG. 39.

In the fourth exemplary embodiment, guy wires 809 are employed to lock the shaft of the instrument in a fixed orientation relative to handle 808. The instrument includes a base 802 rigidly attached to handle 808. Tie down 804 includes an axial bore for slidably and rotatably receiving cylinder 803. Cylinder 803 is rigidly fixed to shaft 116. In this particular embodiment, three separate guy wires 809 are used, but in other embodiments fewer or more guy wires may be used. As best seen in FIG. 39, each of the three guy wires 809 (only one of which is shown for clarity) has one end connected to a wire termination hole 804A in tie down 804, spans proximally to a guy wire bole 802A located in base 802, passes radially inward through locking hole 805A in locking slider 805, radially across locking slider 805 to another locking hole 805A located on the opposite side of locking slider 805, radially outward through another guy wire hole 802A in base 802, and distally back to another wire termination hole 804A in tie down 804. When knob 806 and locking slider 805 are moved to a distal position (not shown) relative to handle 808 and base 802, guy wires 809 may freely move through holes 802A in base 802 which align with holes 805a in locking slider 805, thereby allowing one side of a guy wire 809 to get longer and the other side to get equally shorter. This arrangement allows handle 808 to articulate relative to the proximal end of shaft 116, consequently causing end effector 102 to articulate relative to the distal end of shaft 116, as previously described. On the other hand, when knob 806 and locking slider 805 are moved to a proximal position as shown in FIG. 39, holes 805A become misaligned with holes 802A and guy wires 809 are pinched between locking slider 80S and base 802. This fixes tie down 804 in whatever orientation it is in when knob 806 and slider 80S are moved, which locks the proximal end of shaft 116 from further articulation until the device is unlocked again.

In alternative embodiments (not shown), a locking member such as locking slider 805 may be configured to lock the guy wires when the member is moved distally rather than when moved proximally. In some embodiments, locking slider 805 or other locking member is not coupled to shaft rotation knob 806 and therefore moves distally and proximally independent therefrom, such that knob 806 is axially fixed.

While the inventive surgical instruments, methods and devices have been described in some detail by way of illustration, such illustration is for purposes of clarity of understanding only. It will be readily apparent to those of ordinary skill and in the art in light of the teachings herein that certain changes and modifications may be made thereto without departing from the spirit and scope of the claims. For example, while the tool embodiments described in here have typically been in the context of tools with an articulating mechanism comprising at least two links, the tension member guide system may be used in an instrument comprising only a single link, a multiplicity of links, and with any number of tension members such as cables, or numbers of cable sets operably connecting the links. Further, the tension member guide system may be used in tools that are absent various features that may be associated with some articulatable instruments, such as handles, rotatability features, and dedicated end effectors. Finally, while the context of the invention is considered to be surgical or medical diagnostic procedures, the instruments described herein may have utility in other non-medical contexts as well.

The invention claimed is:

1. A method of using an articulation tool, the method comprising:
    driving movement of a proximal link of the articulation tool, wherein movement of the proximal link about a proximal first axis causes corresponding movement of a distal link of the articulation tool about a distal first axis and movement of the proximal link about a proximal second axis perpendicular to the proximal first axis causes corresponding movement of the distal link about a distal second axis perpendicular to the distal first axis, wherein the articulation tool comprises:
        an elongated shaft extending along an elongated shaft longitudinal axis between the proximal link and the distal link;
        a first lock configured to prevent pivoting motion of the elongated shaft relative to the proximal link about the proximal first axis while allowing pivoting motion of the elongated shaft relative to the proximal link about the proximal second axis; and
        a second lock configured to prevent pivoting motion of the elongated shaft relative to the proximal link about the proximal second axis while allowing pivoting motion of the elongated shaft relative to the proximal link about the proximal first axis;
    adjusting the first lock between an unlocked configuration in which the proximal link and the distal link are movable with respect to the elongated shaft about the proximal and distal first axes, respectively, and a locked configuration in which the proximal link and the distal link are held in a fixed orientation with respect to the elongated shaft about the proximal and distal first axes, respectively;
    adjusting the second lock between an unlocked configuration in which the proximal link and the distal link are movable with respect to the elongated shaft about the proximal and distal second axes, respectively, and a locked configuration in which the proximal link and the distal link are held in a fixed orientation with respect to the elongated shaft about the proximal and distal second axes, respectively; and
    driving rotation of the elongated shaft about the elongated shaft longitudinal axis while the first and second locks are in the locked configuration such that the proximal link and the distal link are angled with respect to the elongated shaft and rotate about respective longitudinal axes during rotation of the elongated shaft.

2. The method of claim 1, wherein the driving rotation of the elongated shaft includes driving rotation of an end effector of the articulation tool, the end effector being coupled to the distal link.

3. The method of claim 1, wherein the distal link is connected to the proximal link by at least one articulation cable such that movement of the proximal link causes the at least one articulation cable to move the distal link.

4. The method of claim 1, wherein both the adjusting the first lock and the adjusting the second lock are performed by actuating a single actuator that simultaneously adjusts the first lock and the second lock.

5. The method of claim 1, wherein both the adjusting the first lock and the adjusting the second lock are performed by actuating a single actuator that sequentially adjusts the first lock and then the second lock.

6. The method of claim 1, wherein the adjusting the first lock is performed by actuating a first actuator and the adjusting the second lock is performed by actuating a second actuator.

7. The method of claim 1, wherein adjusting the first lock between the unlocked configuration and the locked configuration comprises engaging a first pin with teeth of a first gear segment.

8. The method of claim 7, wherein adjusting the second lock between the unlocked configuration and the locked configuration comprises engaging a second pin with teeth of a second gear segment.

9. The method of claim 8, wherein a rotation axis of the first gear segment is parallel to the proximal first axis and wherein a rotation axis of the second gear segment is parallel to the proximal second axis.

10. The method of claim 9, wherein the first pin and the second pin are substantially parallel.

11. An articulation tool, comprising:
    a proximal link;
    a distal link, wherein movement of the proximal link about a proximal first axis causes corresponding movement of the distal link about a distal first axis and movement of the proximal link about a proximal second axis perpendicular to the proximal first axis causes corresponding movement of the distal link about a distal second axis perpendicular to the distal first axis;
    an elongated shaft extending along an elongated shaft longitudinal axis between the proximal link and the distal link;
    a first lock having an unlocked configuration in which the proximal link and the distal link are movable with respect to the elongated shaft about the proximal and distal first axes, respectively, and a locked configuration in which the proximal link and the distal link are held in a fixed orientation with respect to the elongated shaft about the proximal and distal first axes, respectively; and a second lock having an unlocked configuration in which the proximal link and the distal link are movable with respect to the elongated shaft about the proximal and distal second axes, respectively, and a locked configuration in which the proximal link and the distal link are held in a fixed orientation with respect to the elongated shaft about the proximal and distal second axes, respectively;

wherein rotation of the elongated shaft about the elongated shaft longitudinal axis while the first and second locks are in the locked configuration and the proximal and distal links are angled with respect to the elongated shaft causes the proximal and distal links to rotate about respective longitudinal axes.

12. The articulation tool of claim 11, further comprising an end effector coupled to the distal link, wherein rotation of the elongated shaft causes rotation of the end effector.

13. The articulation tool of claim 11, further comprising at least one articulation cable extending between the proximal link and the distal link such that movement of the proximal link causes the at least one articulation cable to move the distal link.

14. The articulation tool of claim 11, further comprising an actuator that simultaneously adjusts the first lock and the second lock between the unlocked configuration and the locked configuration.

15. The articulation tool of claim 11, further comprising an actuator that sequentially adjusts the first lock between the unlocked configuration and the locked configuration and then adjusts the second lock between the unlocked configuration and the locked configuration.

16. The articulation tool of claim 11, further comprising a first actuator configured to adjust the first lock between the unlocked configuration and the locked configuration and a second actuator configured to adjust the second lock between the unlocked configuration and the locked configuration.

17. The articulation tool of claim 11, wherein the first lock comprises a first pin engageable with teeth of a first gear segment.

18. The articulation tool of claim 17, wherein the second lock comprises a second pin engageable with teeth of a second gear segment.

19. The articulation tool of claim 18, wherein the first gear segment has an axis of rotation parallel to the proximal first axis and the second gear segment has an axis of rotation parallel to the proximal second axis.

20. The articulation tool of claim 19, wherein the first pin and the second pin are substantially parallel.

* * * * *